United States Patent
Satou et al.

(10) Patent No.: US 8,765,011 B2
(45) Date of Patent: Jul. 1, 2014

(54) FLUOROVINYL DERIVATIVE, LIQUID CRYSTAL COMPOSITION AND LIQUID CRYSTAL DISPLAY DEVICE

(75) Inventors: Teizi Satou, Ichihara (JP); Yasuyuki Goto, Tokyo (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 13/468,779

(22) Filed: May 10, 2012

(65) Prior Publication Data

US 2012/0286199 A1 Nov. 15, 2012

(30) Foreign Application Priority Data

May 10, 2011 (JP) .................. 2011-105027

(51) Int. Cl.
*C09K 19/06* (2006.01)
*C09K 19/52* (2006.01)
*C09K 19/34* (2006.01)
*C09K 19/32* (2006.01)
*C09K 19/30* (2006.01)
*C09K 19/12* (2006.01)
*C09K 19/00* (2006.01)
*C07C 17/00* (2006.01)
*C07C 23/00* (2006.01)
*C07C 19/00* (2006.01)
*C07C 21/00* (2006.01)

(52) U.S. Cl.
USPC ............ 252/299.6; 252/299.01; 252/299.61; 252/299.62; 252/299.63; 252/299.66; 428/1.1; 428/1.3; 570/101; 570/181; 570/186

(58) Field of Classification Search
USPC ............... 252/299.01, 299.6, 299.61, 299.62, 252/299.63, 299.66; 428/1.1, 1.3; 570/101, 570/181, 186; 349/182
See application file for complete search history.

(56) References Cited

U.S. PATENT DOCUMENTS

| | | | |
|---|---|---|---|
| 4,565,425 A | 1/1986 | Petrzilka et al. | |
| 5,183,587 A | 2/1993 | Kitano et al. | |
| 5,328,642 A * | 7/1994 | Rieger et al. | 252/299.63 |
| 6,180,027 B1 | 1/2001 | Kato et al. | |
| 6,207,075 B1 * | 3/2001 | Muraoka et al. | 252/299.63 |
| 6,207,076 B1 * | 3/2001 | Koga et al. | 252/299.63 |
| 2004/0006235 A1 | 1/2004 | Pauluth | |

FOREIGN PATENT DOCUMENTS

JP 09-291048 11/1997

* cited by examiner

*Primary Examiner* — Geraldina Visconti
(74) *Attorney, Agent, or Firm* — Hogan Lovells US LLP

(57) ABSTRACT

To provide a liquid crystal compound having general physical properties required for the compound, namely, a high stability to heat, light and so forth, a small viscosity, a refractive index anisotropy value having a suitable magnitude, a dielectric constant anisotropy value having a suitable magnitude and steep electro-optical characteristics, a wide temperature range of a nematic phase, and an excellent compatibility with other liquid crystal compounds, in particular, a liquid crystal compound having a wide temperature range of the nematic phase; the compound is represented by formula (1):

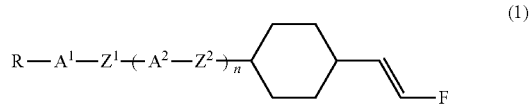

(1)

wherein R is alkenyl having 2 to 20 carbons; ring $A^1$ and ring $A^2$ are independently 1,4-cyclohexylene, or 1,4-phenylene in which at least one of hydrogen may be replaced by fluorine; $Z^1$ and $Z^2$ are independently a single bond, —$CH_2CH_2$—, —CH=CH—, —$CH_2O$— or —$OCH_2$—; and n is 0 or 1.

14 Claims, No Drawings

FLUOROVINYL DERIVATIVE, LIQUID CRYSTAL COMPOSITION AND LIQUID CRYSTAL DISPLAY DEVICE

This is a Non-Provisional application, which claims priority to Japanese Patent Application No. 2011-105027, filed on May 10, 2011; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The invention relates to a new liquid crystal compound and a new liquid crystal composition both having a feature of a wide nematic range. More specifically, the invention relates to a new liquid crystal compound having a wide temperature range of a nematic phase, a low viscosity and a good compatibility with other liquid crystal compounds, and further having a refractive index anisotropy value and a dielectric anisotropy value both having a suitable magnitude, and allowing demonstration of high-speed response characteristics when used for a liquid crystal display device, and also relates to a liquid crystal composition containing the compound, and comprises containing the liquid crystal composition.

BACKGROUND ART

A display device using a liquid crystal compound has been widely used for a display for a watch, a calculator, a word processor and so forth, wherein, in the invention, a term "liquid crystal compound" is used as a generic term for a compound showing a liquid crystal phase, and a compound showing no liquid crystal phase but being useful as a constituent of a liquid crystal composition. The display devices utilize a refractive index anisotropy, a dielectric anisotropy and so forth of the liquid crystal compound.

The liquid crystal phase includes a nematic phase, a smectic phase and a cholesteric phase. A product utilizing the nematic phase has most widely been used. Moreover, a display mode includes a dynamic scattering (DS) mode, a deformation of aligned phase (DAP) mode, a guest/host (GH) mode, a twisted nematic (TN) mode, a super twisted nematic (STN) mode, a thin film transistor (TFT) mode, a vertical alignment (VA) mode, an in-plane switching (IPS) mode and a polymer sustained alignment (PSA) mode.

The liquid crystal compound used according to the display modes should show the liquid crystal phase in a wide temperature range centering on room temperature, be sufficiently stable under conditions in which the display device is used, and have sufficient characteristics for driving the display device. However, no single liquid crystal compound satisfying the conditions has been found out so far.

Therefore, a liquid crystal composition with required characteristics is actually prepared by mixing several kinds to several tens of kinds of liquid crystal compounds. The liquid crystal compositions are required to be stable to moisture, light, heat and air ordinarily present under the conditions in which the display device is used, to be also stable to an electric field and electromagnetic radiation, and to be furthermore chemically stable to a compound to be mixed. Moreover, the liquid crystal composition is needed to have suitable values of physical properties such as a refractive index anisotropy ($\Delta n$) value and a dielectric anisotropy ($\Delta \in$) value depending on the display mode and a shape of the display device. Furthermore, each component in the liquid crystal composition importantly has a good solubility with each other.

In order to perform a good liquid crystal display, a cell thickness of a liquid crystal display device constituting the good liquid crystal display and a $\Delta n$ value of a liquid crystal material to be used are preferably constant (E. Jakeman et al., Phys. Lett., 39A., p. 69 (1972)). Moreover, a response speed of the liquid crystal display device is inversely proportional to a square of thickness of a cell to be used. Therefore, a liquid crystal composition having a large $\Delta n$ value should be available in order to manufacture a liquid crystal display device allowing a high speed response and also allowing application to displaying moving images and so forth. A variety of compounds have been developed as a liquid crystal single component having the large $\Delta n$ value. In general, such a compound having the large $\Delta n$ value is hard to use as a constituent of a liquid crystal composition having good electric characteristics because the compound has a highly conjugated molecular structure and tends to have a poor compatibility with other liquid crystal compounds. Furthermore, a high stability is required for a liquid crystal compound used as a constituent of a liquid crystal composition for a liquid crystal display device having a thin film transistor mode and so forth in which a high insulation (specific resistance) is required.

In order to solve the problems, a variety of compounds having a fluorovinyl group, a difluorovinyl group or an alkenyl group in a side chain have been synthesized as a compound that can be used for the liquid crystal display device. For example, compounds represented by formulas (S-1) to (S-3) are disclosed in Patent literature No. 1, a compound represented by formula (S-4) is disclosed in Patent literature No. 2, a compound represented by formula (S-5) is disclosed in Patent literature No. 3, a compound represented by formula (S-6) is disclosed in Patent literature No. 4, and a compound represented by formula (S-7) is disclosed in Patent literature No. 5.

However, the compounds represented by formulas (S-1), (S-2), (S-4) and (S-6) have only 46° C. in the widest temperature range of the nematic phase, and no nematic phase is developed in the compounds represented by formulas (S-3) and (S-7). No physical properties of the compound represented by formula (S-5) are disclosed. In any case, the known compounds cannot simultaneously satisfy a wide temperature range of the nematic phase, a low viscosity and a good compatibility with other liquid crystal compounds.

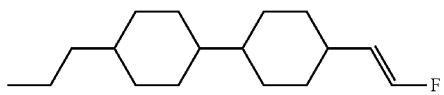

(S-1)

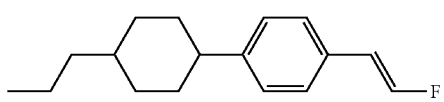

(S-2)

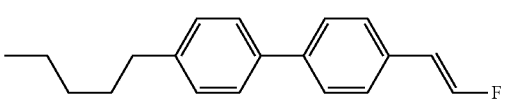

(S-3)

-continued

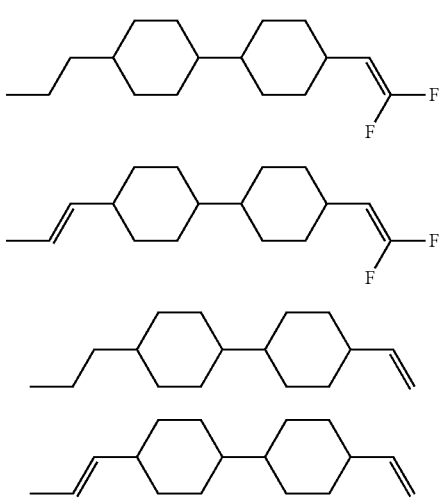

(S-4)
(S-5)
(S-6)
(S-7)

CITATION LIST

Patent Literature

Patent literature No. 1: JP H02-184642 A.
Patent literature No. 2: JP H09-291048 A.
Patent literature No. 3: JP H10-45639 A.
Patent literature No. 4: JP S59-176221 A.
Patent literature No. 5: JP 2003-286208 A.

SUMMARY OF INVENTION

Technical Problem

An aim of the invention is to provide a new liquid crystal compound having a wide temperature range of a nematic phase, a low viscosity and a good compatibility with other liquid crystal compounds, and also having a refractive index anisotropy value and a dielectric anisotropy value both having a suitable magnitude, and allowing demonstration of high-speed response characteristics when used for a liquid crystal display device, and to provide a liquid crystal composition containing the compound, and a liquid crystal display device constituted by using the liquid crystal composition.

Solution to Problem

The inventors of the invention have diligently continued to conduct research for overcoming the disadvantages of the background art, as a result, have found that cyclohexane compound (1) having fluorovinyl and alkenyl at both ends has a very wide temperature range of a nematic phase, a low viscosity and a good compatibility with other liquid crystal compounds, and that the compound described above is suitable for a liquid crystal display device, in particular, a currently widely used liquid crystal display device having a TN mode, an STN mode, a TFT mode or the like, and thus completed the invention.

Specifically, the invention concerns a compound represented by formula (1):

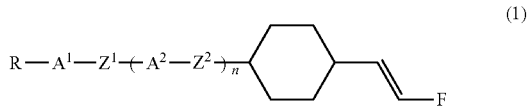

(1)

wherein R is alkenyl having 2 to 20 carbons; ring $A^1$ and ring $A^2$ are independently 1,4-cyclohexylene, or 1,4-phenylene in which at least one of hydrogen may be replaced by fluorine; $Z^1$ and $Z^2$ are independently a single bond, $-CH_2CH_2-$, $-CH=CH-$, $-CH_2O-$ or $-OCH_2-$; and n is 0 or 1.

The invention also concerns a liquid crystal composition containing at least one of the compounds.

The invention further concerns a liquid crystal display device containing at least one of the compositions.

The invention includes the items 1 to 14 described below.

Item 1.

A compound represented by formula (1):

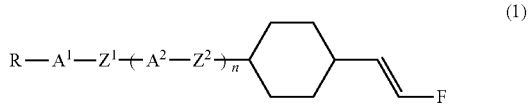

(1)

wherein R is alkenyl having 2 to 20 carbons; ring $A^1$ and ring $A^2$ are independently 1,4-cyclohexylene, or 1,4-phenylene in which at least one of hydrogen may be replaced by fluorine; $Z^1$ and $Z^2$ are independently a single bond, $-CH_2CH_2-$, $-CH=CH-$, $-CH_2O-$ or $-OCH_2-$; and n is 0 or 1.

Item 2.

The compound according to item 1, wherein, in formula (1), R is alkenyl having 2 to 20 carbons; and ring $A^1$ is 1,4-cyclohexylene, $Z^2$ is a single bond, and n is 0.

Item 3.

A liquid crystal composition containing at least one compound according to item 1 or 2.

Item 4.

The liquid crystal composition according to item 3, further containing at least one compound selected from the group of compounds represented by formulas (2), (3) and (4):

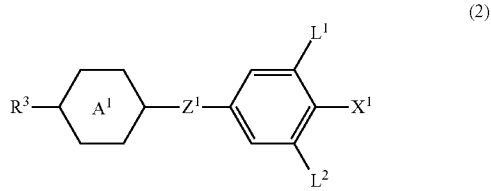

(2)

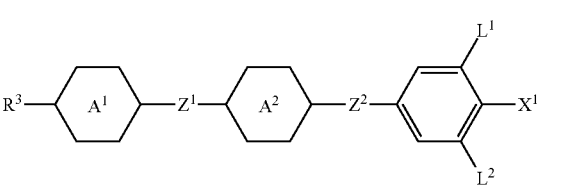

(3)

(4)

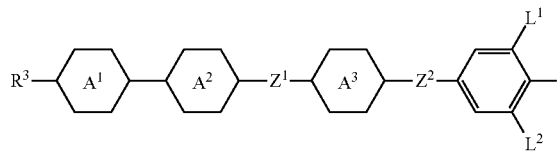

wherein $R^3$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^1$ is fluorine, chlorine, —$OCF_3$—, —$OCHF_2$—, —$CF_3$, —$CHF_2$, —$CH_2F$, —$OCF_2CHF_2$ or —$OCF_2CHFCF_3$;

ring $A^1$, ring $A^2$ and ring $A^3$ are independently 1,4-cyclohexylene, 1,3-dioxane-2,5-diyl, pyrimidine-2,5-diyl, 1-pyran-2,5-diyl, or 1,4-phenylene in which at least one of hydrogen may be replaced by fluorine;

$Z^1$ and $Z^2$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^1$ and $L^2$ are independently hydrogen or fluorine.

Item 5.

The liquid crystal composition according to item 3, further containing at least one compound selected from the group of compounds represented by formula (5):

(5)

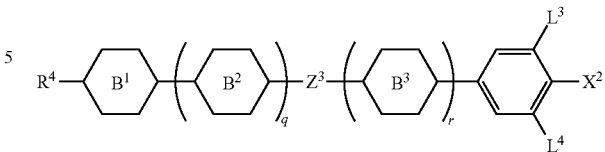

wherein $R^4$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^2$ is —C≡N or —C≡C—C≡N;

ring $B^1$, ring $B^2$ and ring $B^3$ are independently 1,4-cyclohexylene, 1,4-phenylene in which at least one of hydrogen may be replaced by fluorine, 1,3-dioxane-2,5-diyl, 1-pyran-2,5-diyl or pyrimidine-2,5-diyl;

$Z^3$ is —$(CH_2)_2$—, —COO—, —$CF_2O$—, —$OCF_2$—, —C≡C—, —$CH_2O$— or a single bond;

$L^3$ and $L^4$ are independently hydrogen or fluorine; and q is 0, 1 or 2, and r is 0 or 1.

Item 6.

The liquid crystal composition according item 3, further containing at least one compound selected from the group of compounds represented by formulas (6), (7), (8), (9), (10) and (11):

(6)

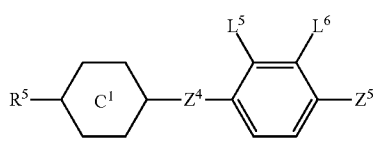

(7)

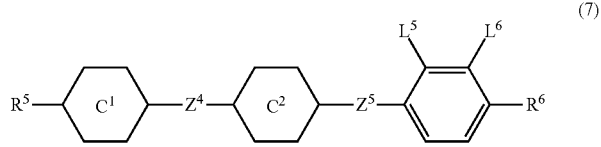

(8)

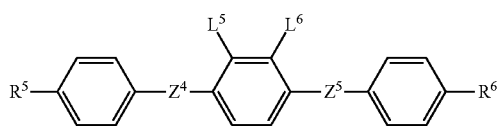

(9)

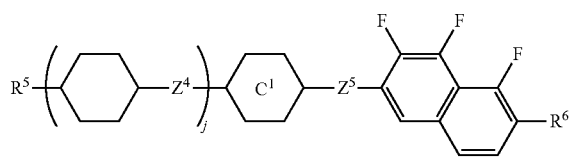

(10)

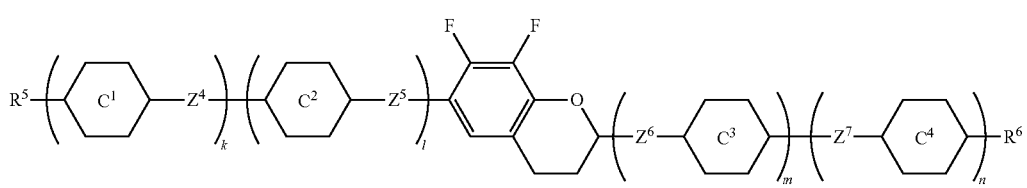

(11)

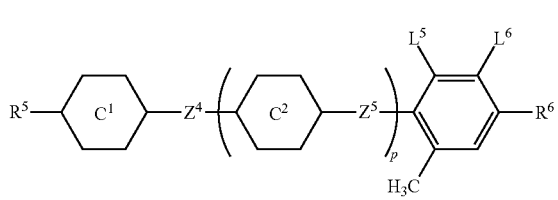

wherein $R^5$ and $R^6$ are independently alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

ring $C^1$, ring $C^2$, ring $C^3$ and ring $C^4$ are independently 1,4-cyclohexylene, 1,4-cyclohexenylene, 1,4-phenylene in which at least one of hydrogen may be replaced by fluorine, 6-pyran-2,5-diyl or decahydro-2,6-naphthalene;

$Z^4$, $Z^5$, $Z^6$ and $Z^7$ are independently —$(CH_2)_2$—, —COO—, —$CH_2O$—, —$OCF_2$—, —$OCF_2(CH_2)_2$— or a single bond;

$L^5$ and $L^6$ are independently fluorine or chlorine; and j, k, l, m, n and p are independently 0 or 1, and a sum of k, l, m and n is 1 or 2.

Item 7.

The liquid crystal composition according to item 3, further containing at least one compound selected from the group of compounds represented by formulas (12), (13) and (14):

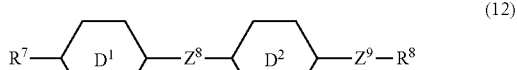

(12)

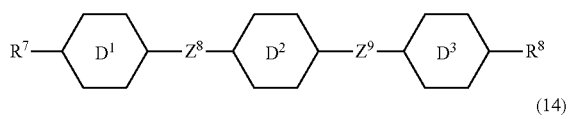

(13)

(14)

wherein $R^7$ and $R^8$ are independently alkyl having 1 to 10 carbons or alkenyl having 2 to 10 carbons, and in the alkyl and the alkenyl, at least one of —$CH_2$— may be replaced by —O— and at least one of hydrogen may be replaced by fluorine, excluding hydrogen in —CH=CHF;

ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^8$ and $Z^9$ are independently —C≡C—, —COO—, —$(CH_2)_2$—, —CH=CH— or a single bond.

Item 8.

The liquid crystal composition according to item 4, further containing at least one compound selected from the group of compounds represented by formula (5) according to item 5.

Item 9.

The liquid crystal composition according to item 4, further containing at least one compound selected from the group of compounds represented by formulas (12), (13) and (14) according to item 7.

Item 10.

The liquid crystal composition according to item 5, further containing at least one compound selected from the group of compounds represented by formulas (12), (13) and (14) according to item 7.

Item 11.

The liquid crystal composition according to item 6, further containing at least one compound selected from the group of compounds represented by formulas (12), (13) and (14) according to item 7.

Item 12.

The liquid crystal composition according to any one of items 3 to 11, further containing at least one optically active compound and/or at least one polymerizable compound.

Item 13.

The liquid crystal composition according to any one of items 3 to 12, further containing at least one antioxidant and/or at least one ultraviolet light absorber.

Item 14.

A liquid crystal display device containing the liquid crystal composition according to any one of items 3 to 13.

Advantageous Effects of Invention

As compared with a publicly known compound having a similar structure, a compound of the invention has a wider temperature range of a nematic phase, a more excellent compatibility with other liquid crystal materials and a lower viscosity. Moreover, as compared with a similar compound, the compound of the invention has a lower threshold voltage and also shows a comparatively lower viscosity. Furthermore, the compound of the invention is sufficiently physically and chemically stable under conditions in which a liquid crystal display device is ordinarily used. The compound is exceptional as a constituent of a nematic liquid crystal composition, and can be suitably used as a constituent of a liquid crystal composition for use in a device having a TN mode, an STN mode, a TFT mode, a VA mode, an IPS mode and a PSA mode.

DESCRIPTION OF EMBODIMENTS

Usage of terms in the specification and claims is as described below. A liquid crystal compound is a generic term for a compound having a liquid crystal phase such as a nematic phase or a smectic phase, and a compound having no liquid crystal phase but being useful as a component of a liquid crystal composition. The liquid crystal compound, the liquid crystal composition and a liquid crystal display device may be abbreviated as "compound," "composition" and "device," respectively. The liquid crystal display device is a generic term for a liquid crystal display panel and a liquid crystal display module. A higher limit of a temperature range of the nematic phase is a phase transition temperature between the nematic phase and an isotropic phase, and may simply be abbreviated as "clearing point" or "maximum temperature." A lower limit of the temperature range of the nematic phase may simply be abbreviated as "minimum temperature." A compound represented by formula (1) may be abbreviated as "compound (1)." The abbreviation may also apply to a compound represented by formula (2) and so forth. In formula (1) to formula (14), symbols such as B, D and E surrounded by a hexagonal shape correspond to ring B, ring D and ring E, respectively. An amount of the compound expressed by percentage is expressed in terms of weight percent (% by weight) based on the total weight of the composition. A plurality of identical symbols such as ring $A^1$, $X^1$ and ring $B^1$ are described in identical or different formulas, and groups selected by the symbols may be identical or different.

Specific examples of alkenyl represented by R in formula (1) include alkenyl such as vinyl, propenyl, butenyl and pentenyl, and alkadienyl such as butadienyl.

Compound (1) of the invention can be obtained by introducing a predetermined group into R in the formula. Such a group can be introduced according to a publicly known general organic synthesis method. Representative synthetic examples include methods as described in New Experimental Chemistry Course (Shin Jikken Kagaku Koza in Japanese), Vol. 14: Synthesis and Reaction of Organic Compound (1978) (Maruzen Co., Ltd.) or Experimental Chemistry Course (Jikken Kagaku Koza in Japanese), 4th edition, Vol. 19 to Vol. 26: Organic Synthesis I to VIII (1991) (Maruzen Co., Ltd.).

With regard to one example of methods for forming a fluorovinyl group, a scheme is first shown, and then the scheme will be explained in step (I) to step (II). In the scheme, R is defined in the same way as described above.

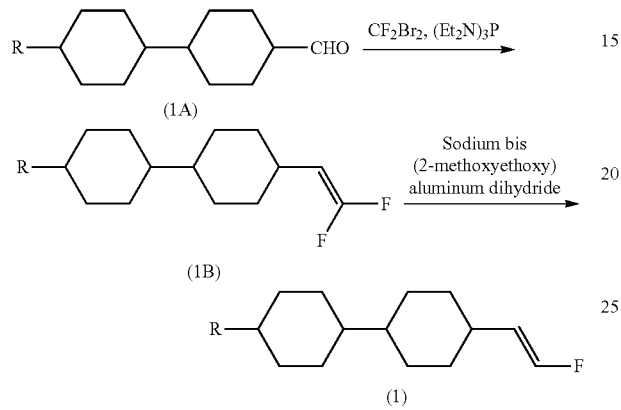

Step (I): Formation of a Difluorovinyl Group

Compound (1B) is prepared by allowing alkenyl compound (1A) prepared according to a publicly known method to react with dibromodifluoromethane in the presence of tris(diethylamino)phosphine.

Step (II): Formation of the Fluorovinyl Group

Fluorovinyl compound (1) is obtained by allowing sodium bis(2-methoxyethoxy)aluminum dihydride to react with difluorovinyl compound (1B).

The liquid crystal composition of the invention is needed to contain compound (1) of the invention as component A. The liquid crystal composition may be a composition containing only component A or a composition of component A and any other component, a name of which is not particularly shown in the specification. A liquid crystal composition having various characteristics according to the invention can be provided by adding to component A a component selected from components B, C, D and E shown below.

As the component to be added to component A, component A is preferably mixed with component B including at least one kind of compound selected from the group of compounds represented by formulas (2), (3) and (4), and/or component C including at least one kind of compound selected from the group of compounds represented by formula (5), and/or component D including at least one kind of compound selected from the group of compounds represented by formulas (6), (7), (8), (9), (10) and (11). Furthermore, component A is mixed with component E including at least one kind of compound selected from the group of compounds represented by formulas (12), (13) and (14), and thus a threshold voltage, a temperature range of the liquid crystal phase, a refractive index anisotropy value and a dielectric anisotropy value, viscosity and so forth can be adjusted.

Moreover, even when each component of the liquid crystal composition to be used in the invention is an analog including an isotopic element of each element, each component has no significant difference in physical characteristics.

Among compounds of component B, suitable examples of compound (2) include compounds (2-1) to (2-16), suitable examples of compound (3) include compounds (3-1) to (3-112), and suitable examples of compound (4) include compounds (4-1) to (4-54).

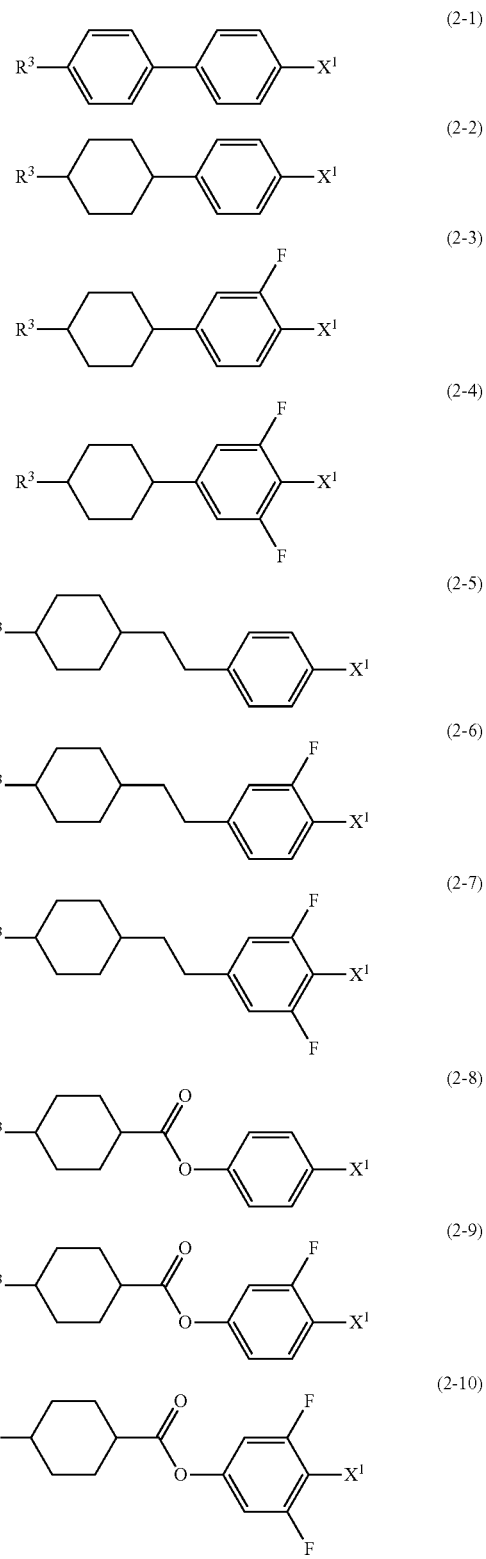

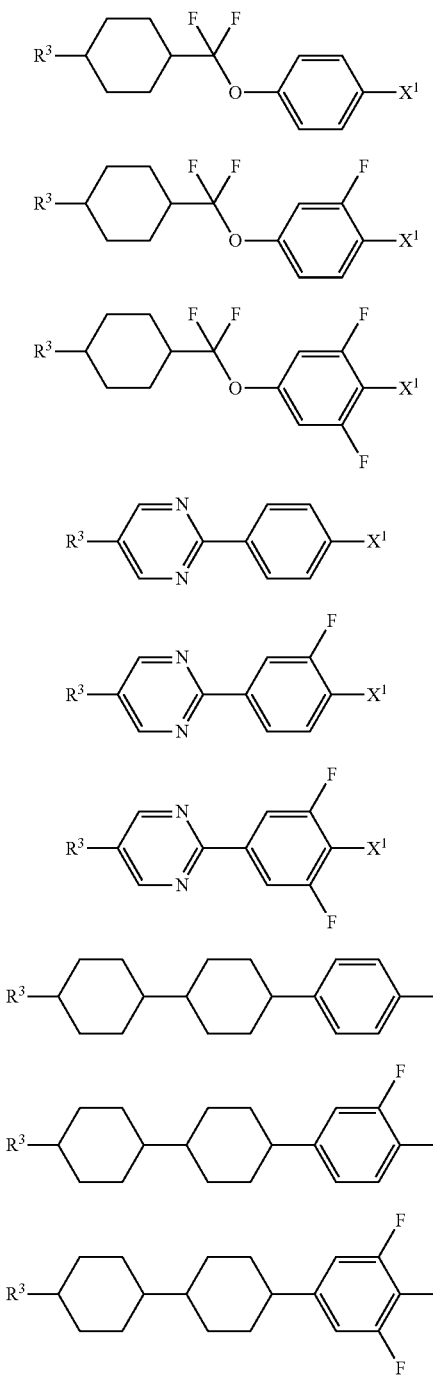
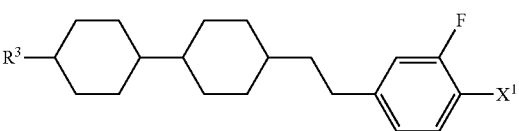
(3-6)
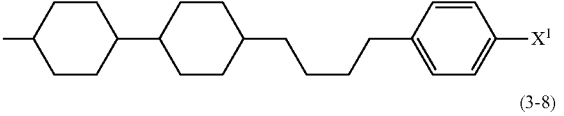
(3-7)
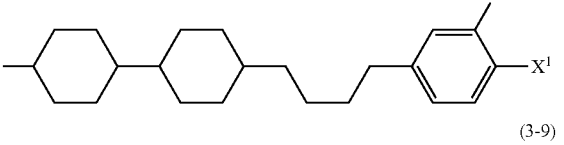
(3-8)
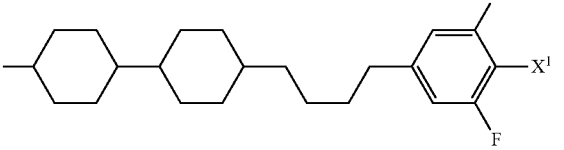
(3-9)
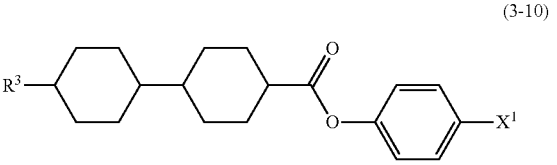
(3-10)
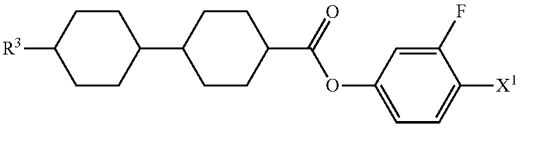
(3-11)
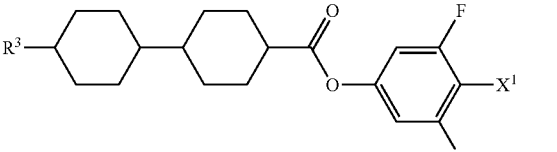
(3-12)
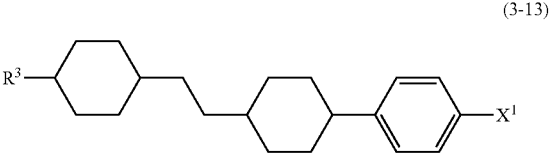
(3-13)
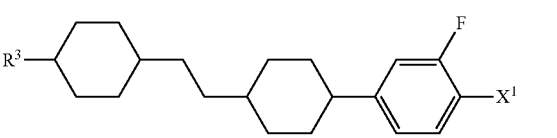
(3-14)

(3-15) 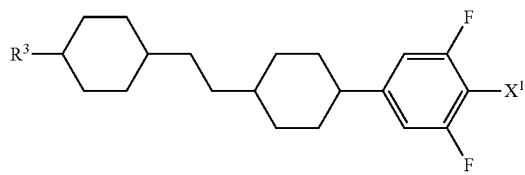
(3-16) 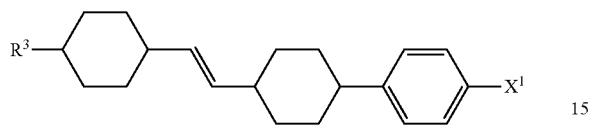
(3-17) 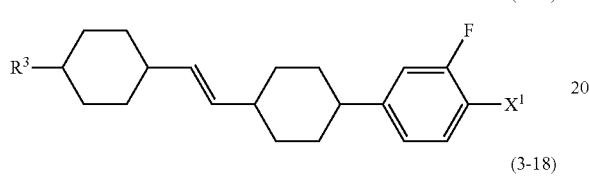
(3-18) 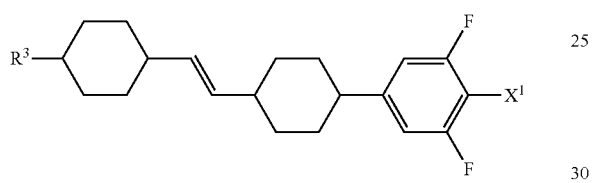
(3-19) 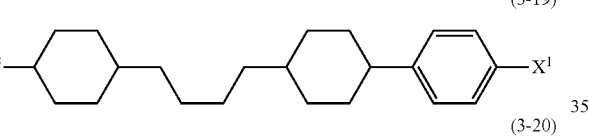
(3-20) 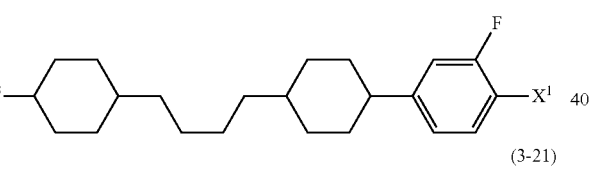
(3-21) 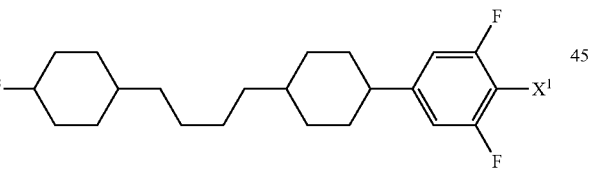
(3-22) 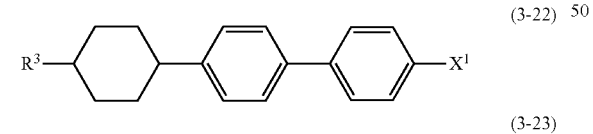
(3-23) 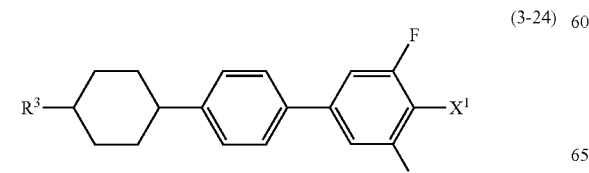
(3-24) 
(3-25) 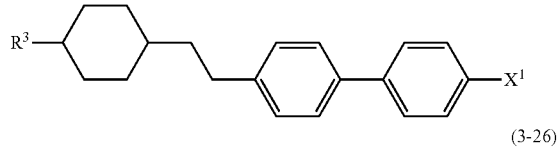
(3-26) 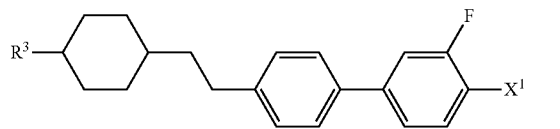
(3-27) 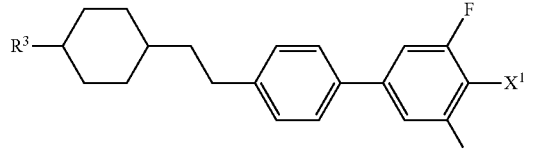
(3-28) 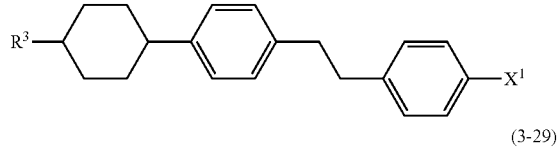
(3-29) 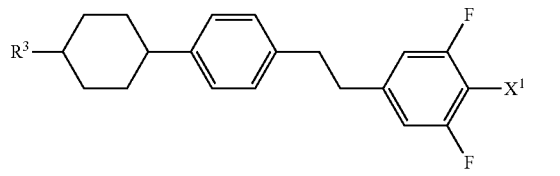
(3-30) 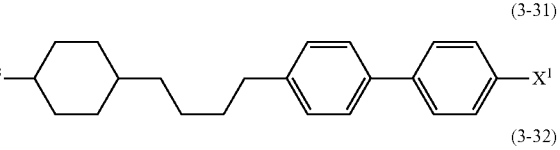
(3-31) 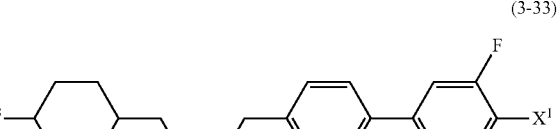
(3-32) 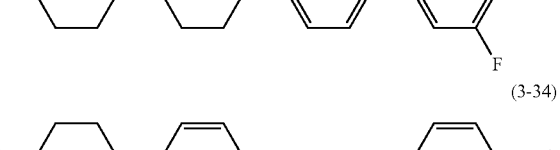
(3-33) 
(3-34) 

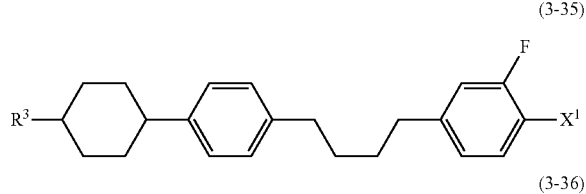
(3-35)
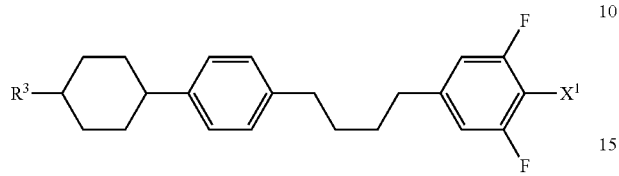
(3-36)
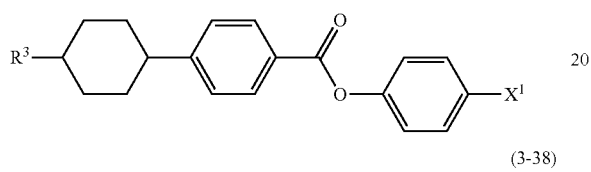
(3-37)
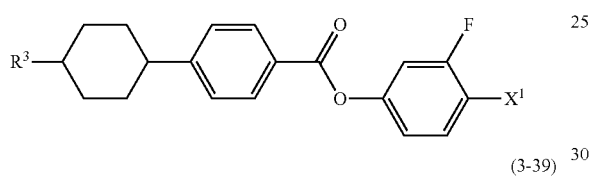
(3-38)
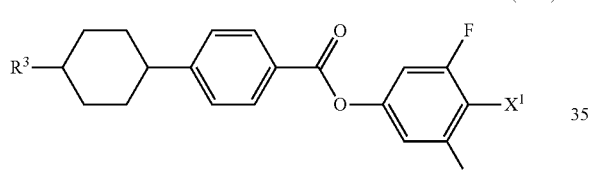
(3-39)
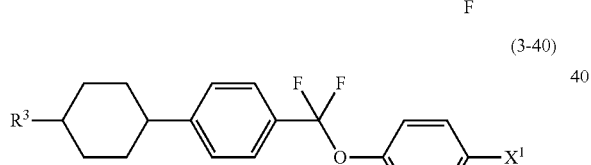
(3-40)
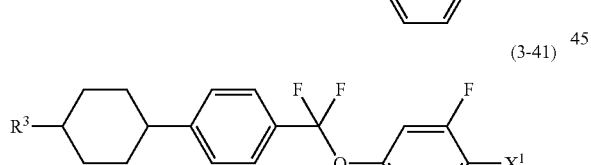
(3-41)
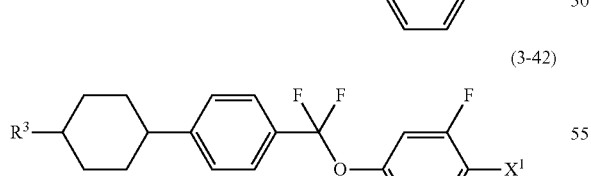
(3-42)
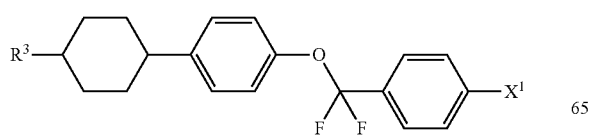
(3-43)
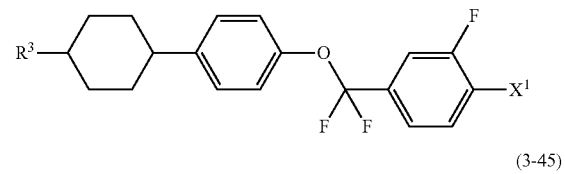
(3-44)
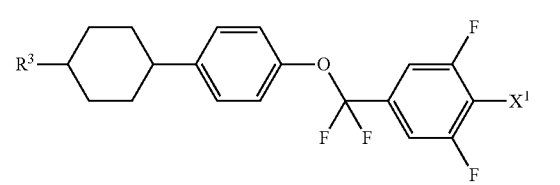
(3-45)
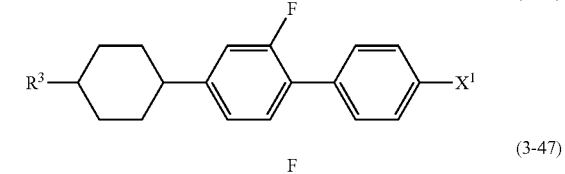
(3-46)
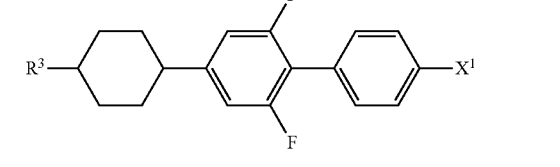
(3-47)
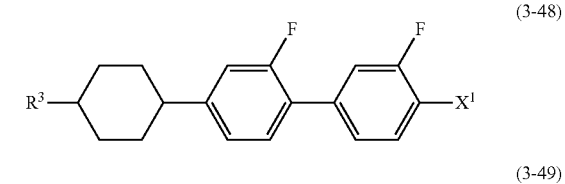
(3-48)
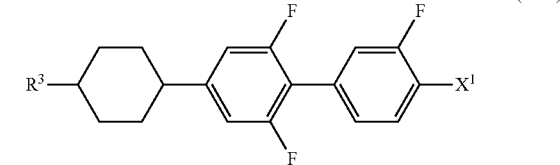
(3-49)
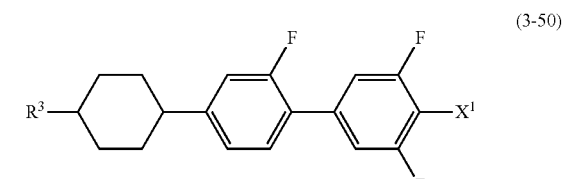
(3-50)
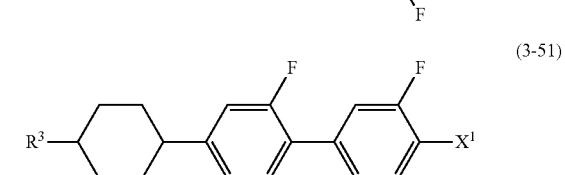
(3-51)
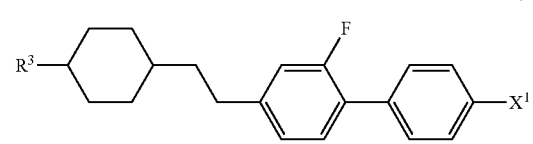
(3-52)

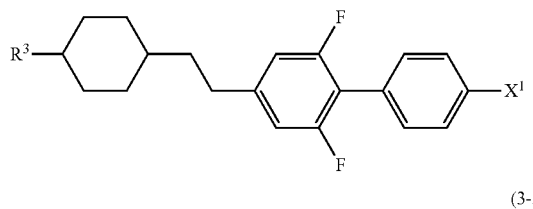
(3-53)
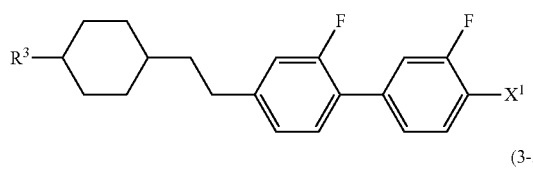
(3-54)
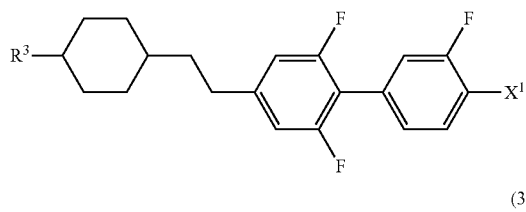
(3-55)
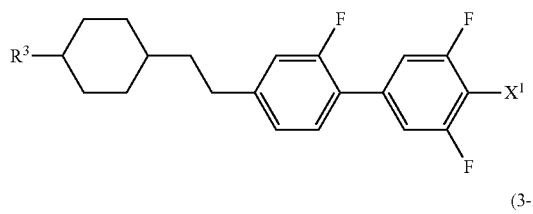
(3-56)
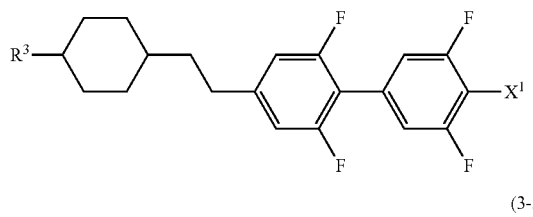
(3-57)
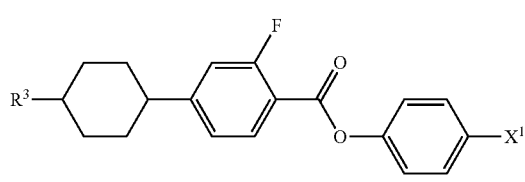
(3-58)
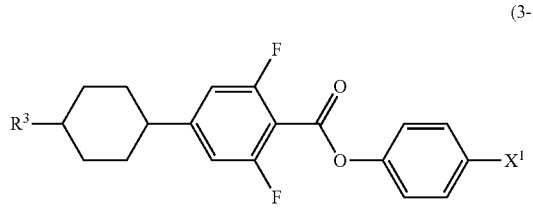
(3-59)
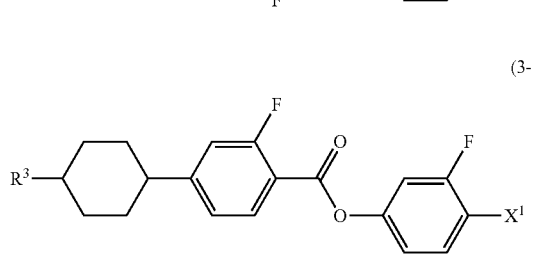
(3-60)
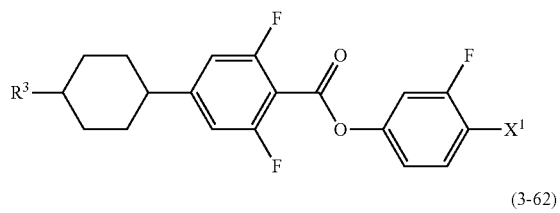
(3-61)
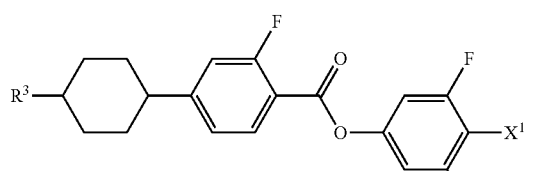
(3-62)
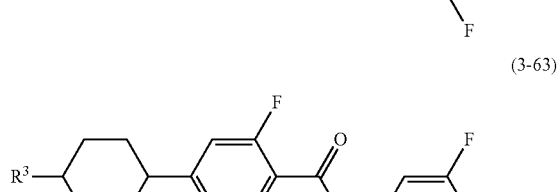
(3-63)
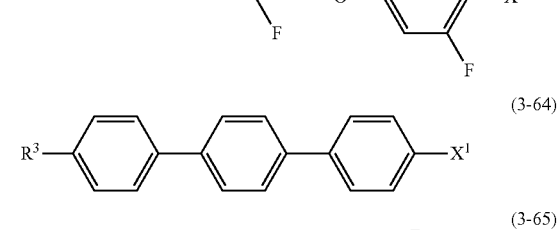
(3-64)
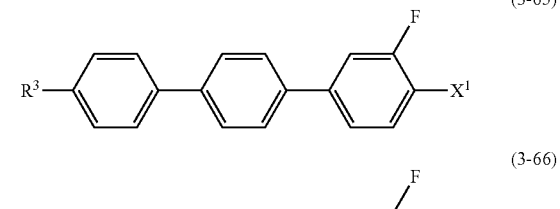
(3-65)
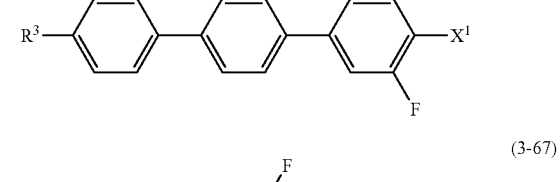
(3-66)
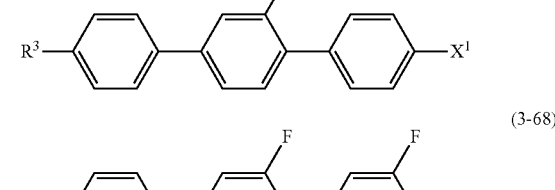
(3-67)
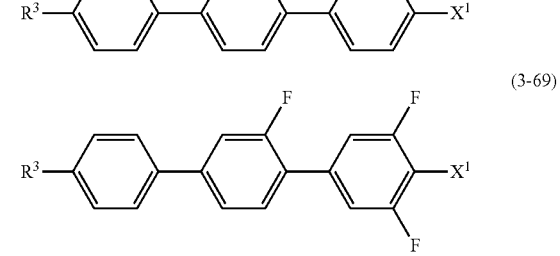
(3-68)
(3-69)

(3-70) 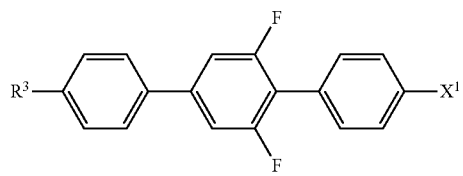
(3-71) 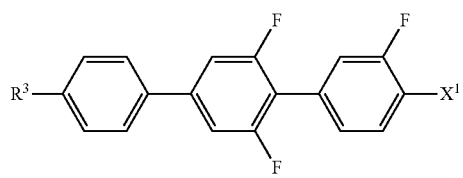
(3-72) 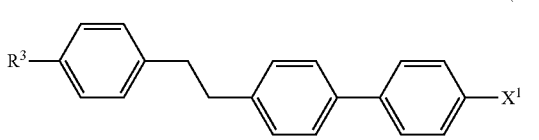
(3-73) 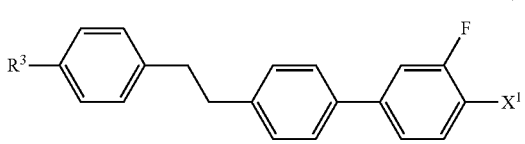
(3-74) 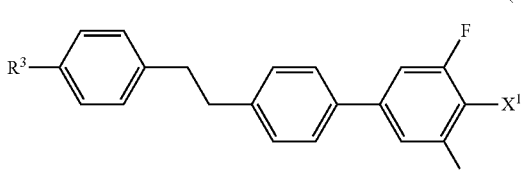
(3-75) 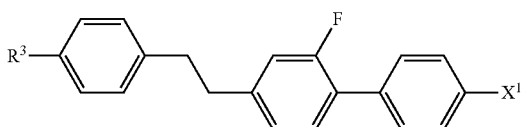
(3-76) 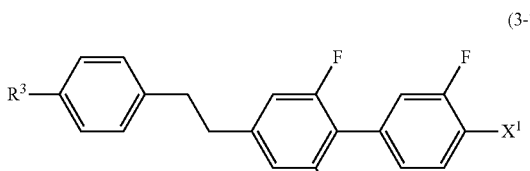
(3-77) 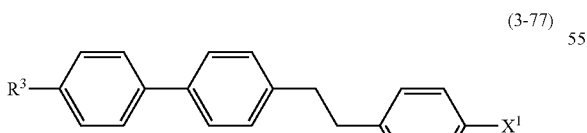
(3-78) 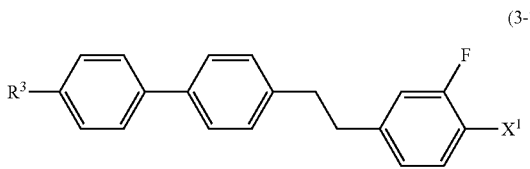
(3-79) 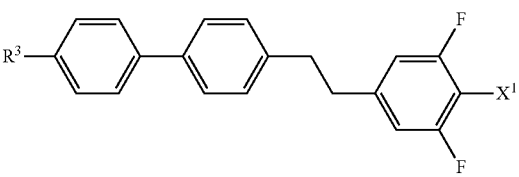
(3-80) 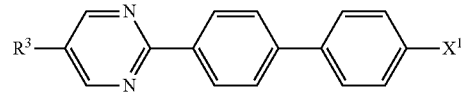
(3-81) 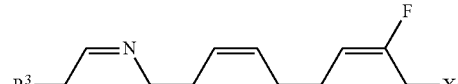
(3-82) 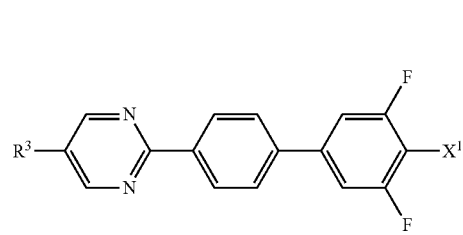
(3-83) 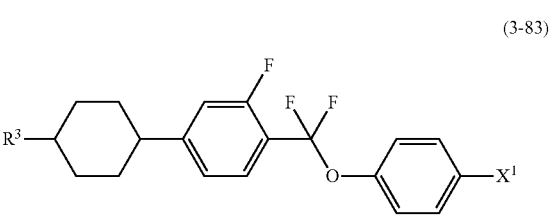
(3-84) 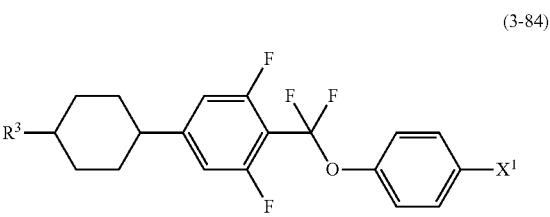
(3-85) 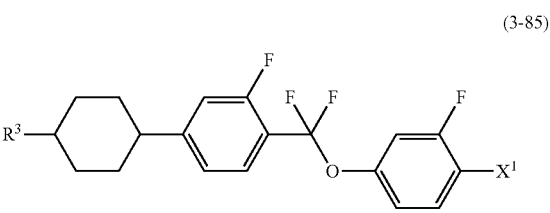
(3-86) 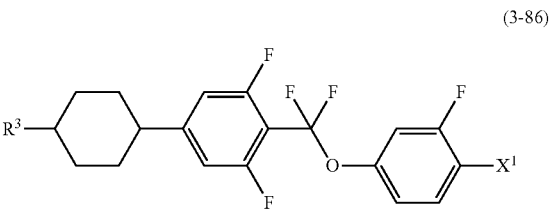

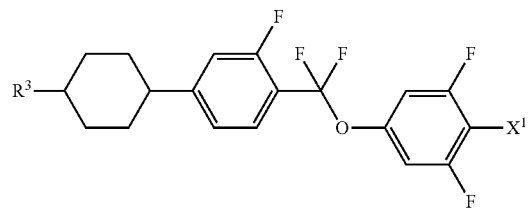
(3-87)
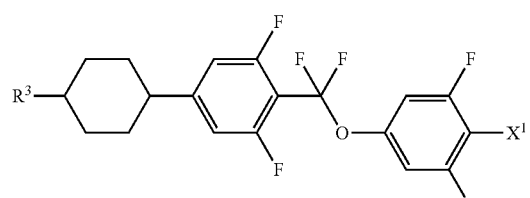
(3-88)
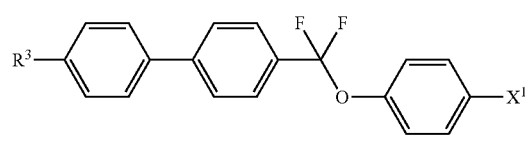
(3-89)
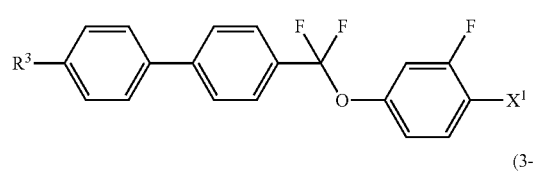
(3-90)
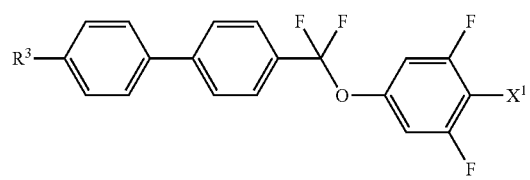
(3-91)
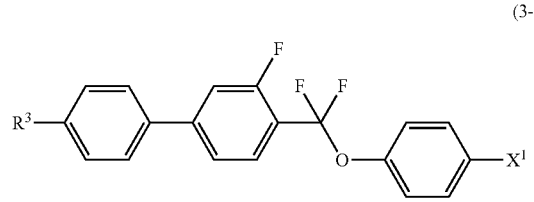
(3-92)
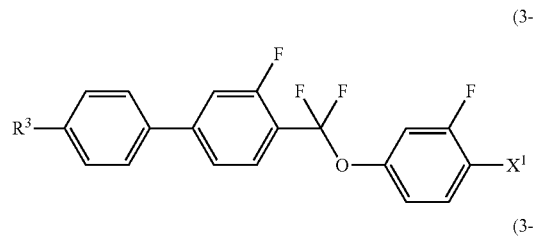
(3-93)
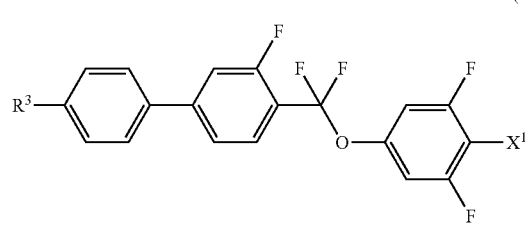
(3-94)
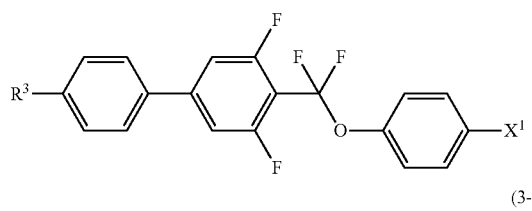
(3-95)
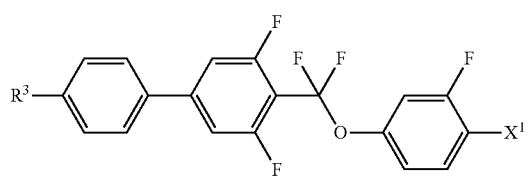
(3-96)
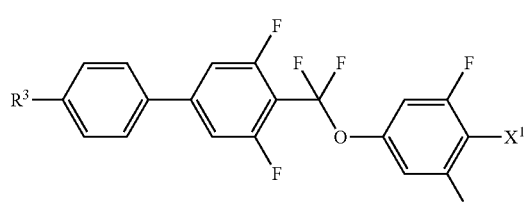
(3-97)
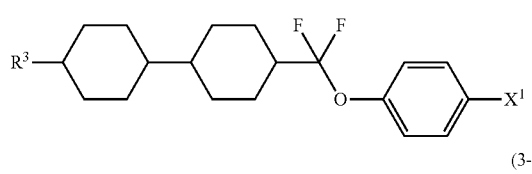
(3-98)
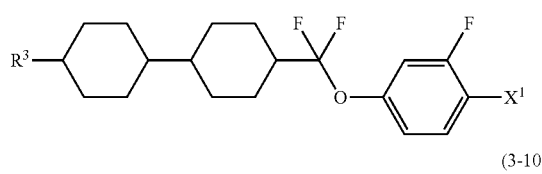
(3-99)
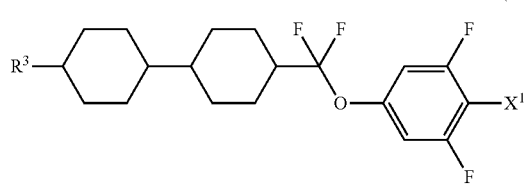
(3-100)
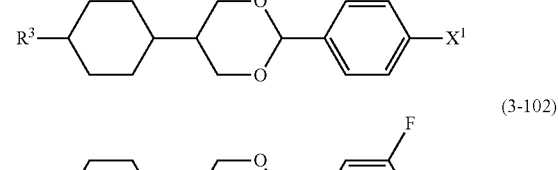
(3-101)
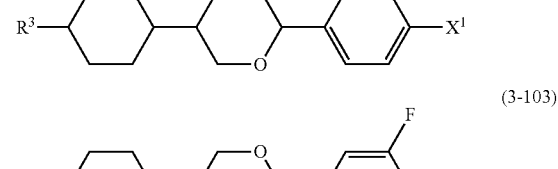
(3-102)
(3-103)

(3-104) 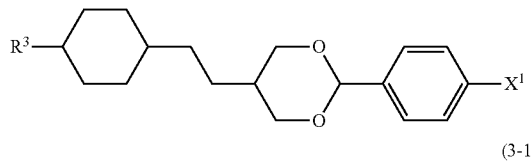
(3-105) 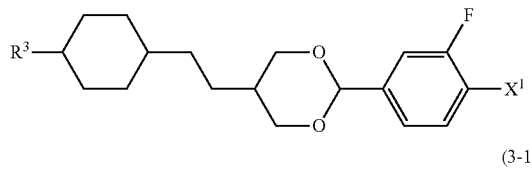
(3-106) 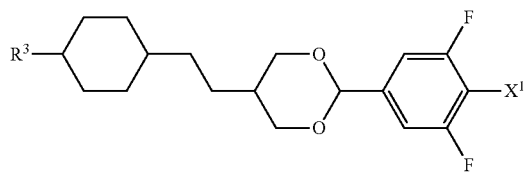
(3-107) 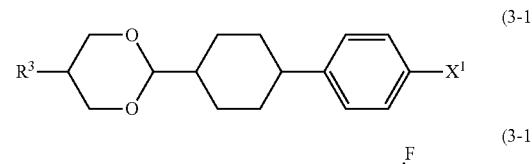
(3-108) 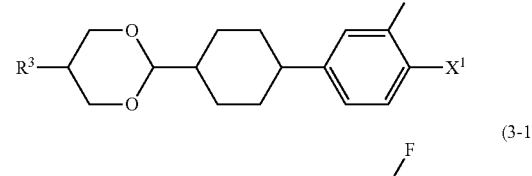
(3-109) 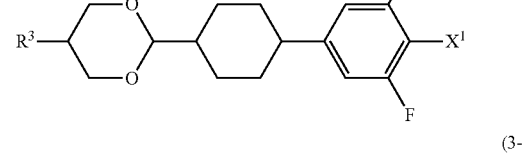
(3-110) 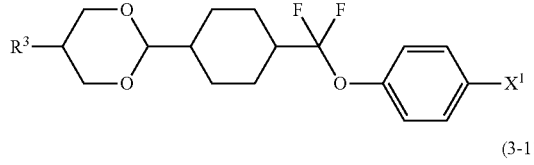
(3-111) 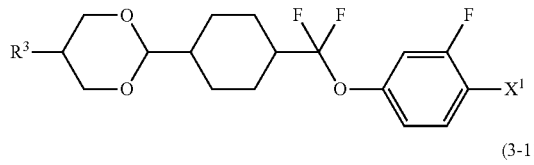
(3-112) 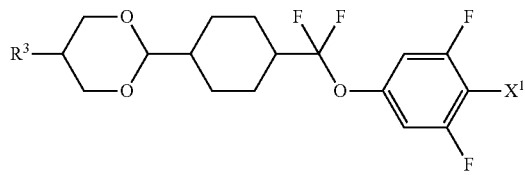
(4-1) 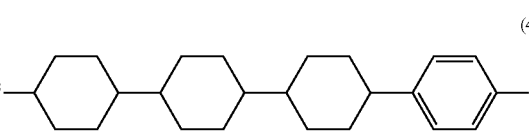
(4-2) 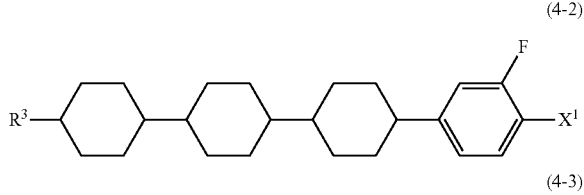
(4-3) 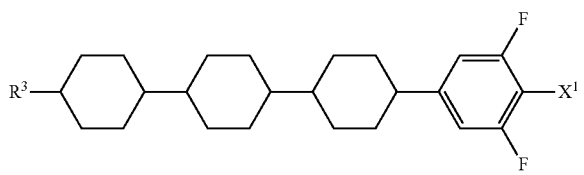
(4-4) 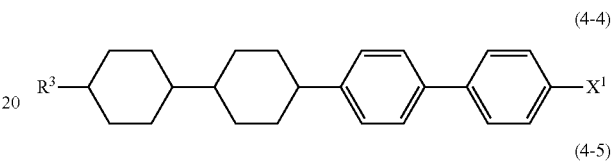
(4-5) 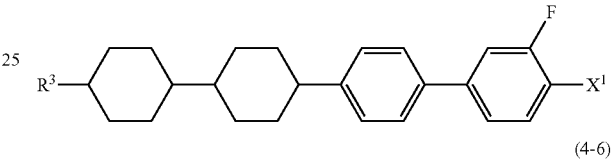
(4-6) 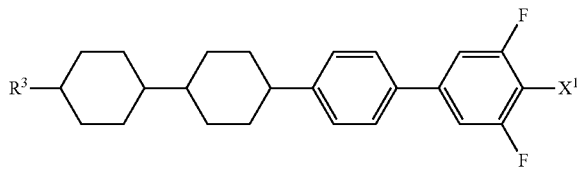
(4-7) 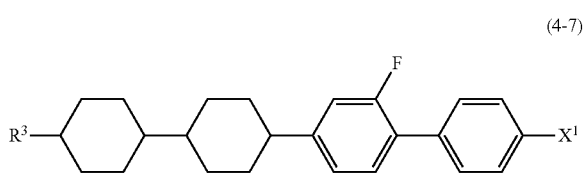
(4-8) 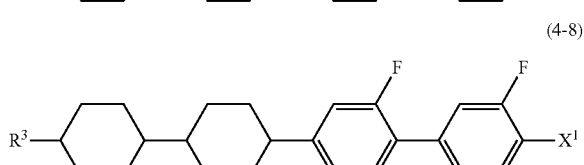
(4-9) 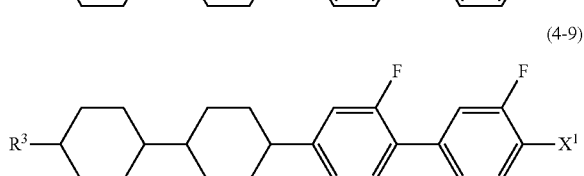
(4-10) 
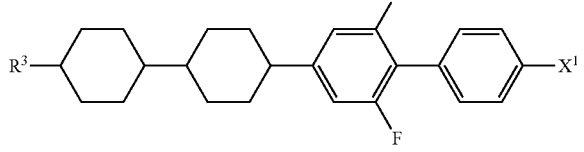

(4-11) 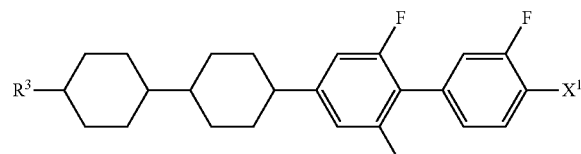
(4-12) 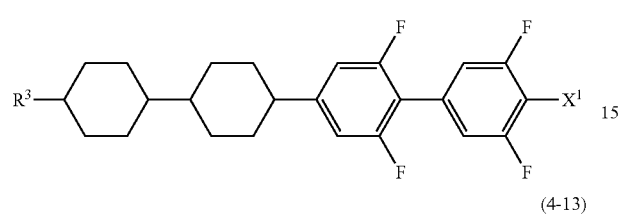
(4-13) 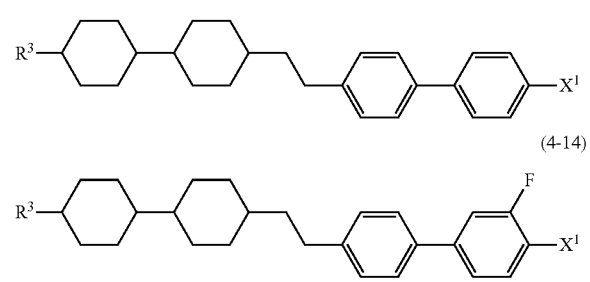
(4-14) 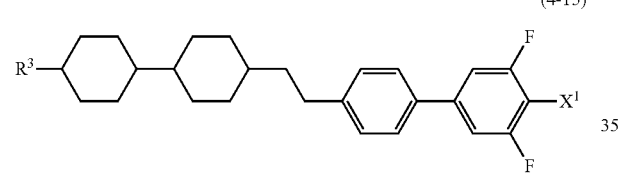
(4-15) 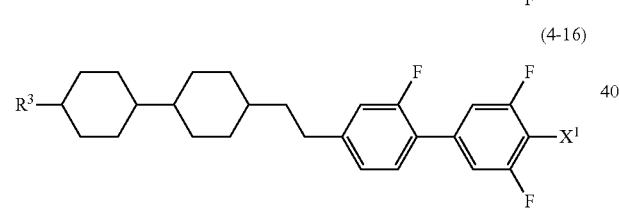
(4-16) 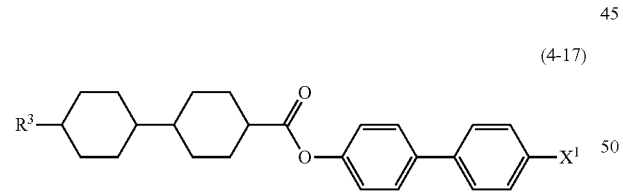
(4-17) 
(4-18) 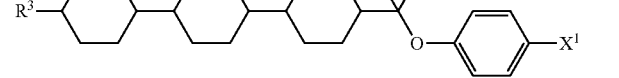
(4-19) 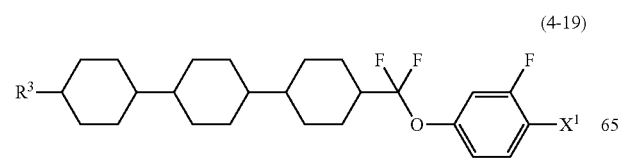
(4-20) 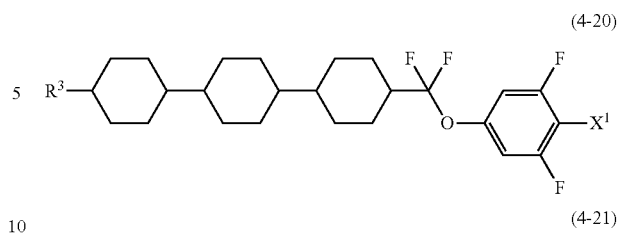
(4-21) 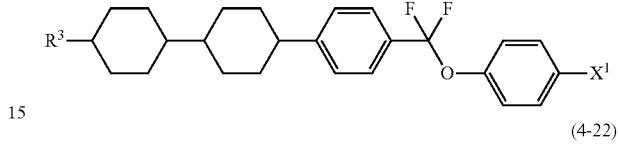
(4-22) 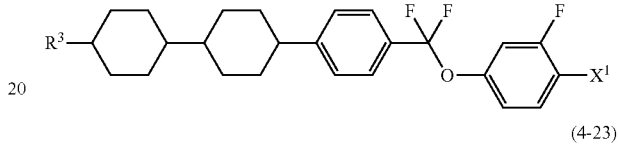
(4-23) 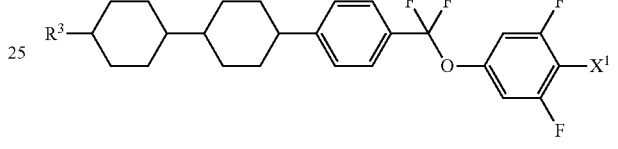
(4-24) 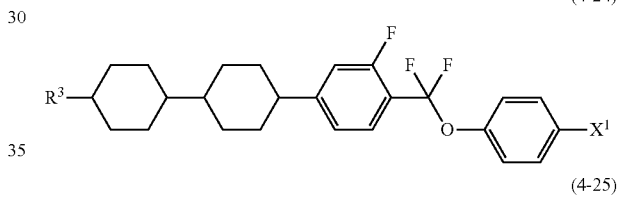
(4-25) 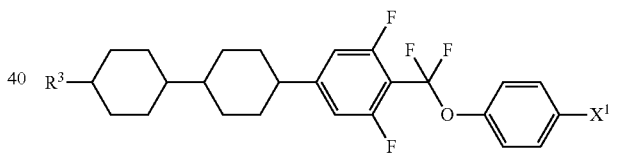
(4-26) 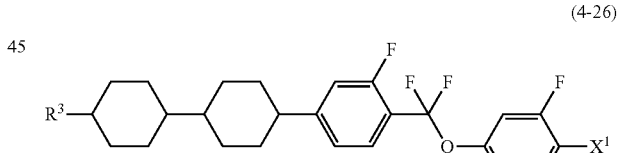
(4-27) 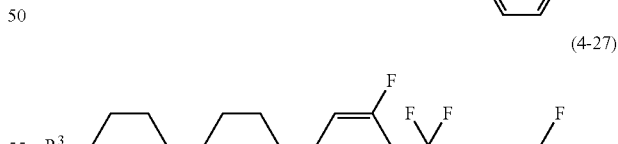
(4-28) 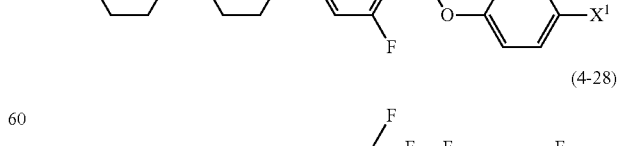
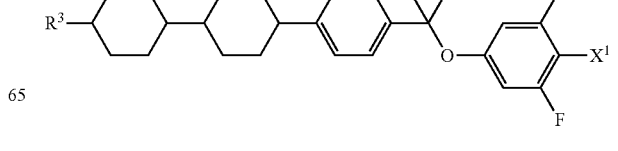

(4-29)
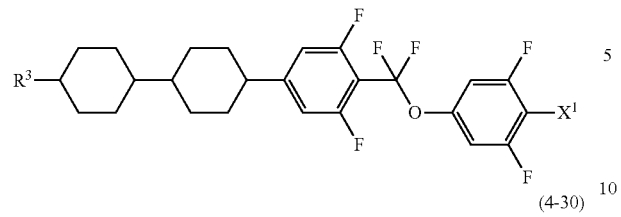
(4-30)
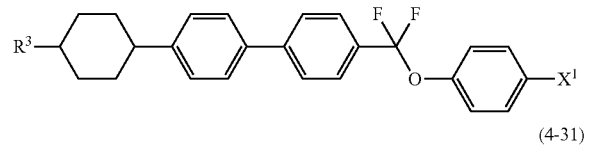
(4-31)
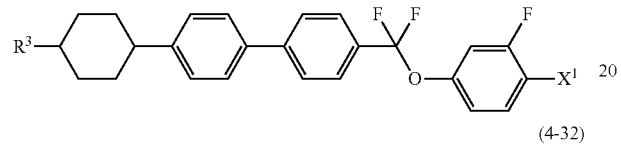
(4-32)
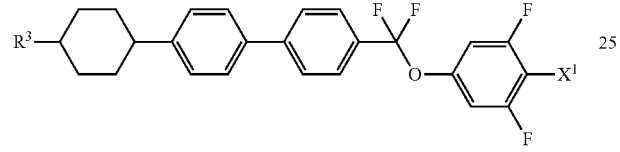
(4-33)
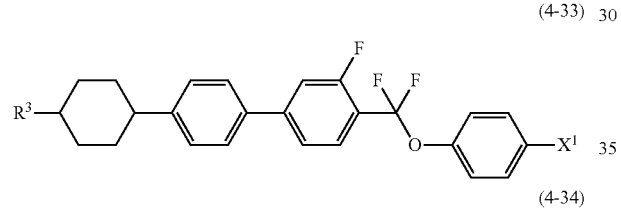
(4-34)
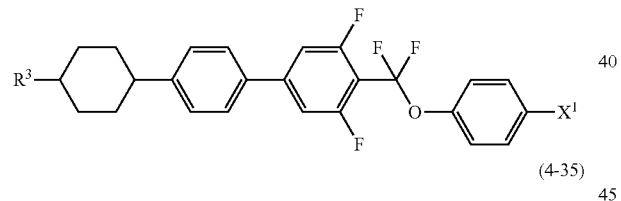
(4-35)
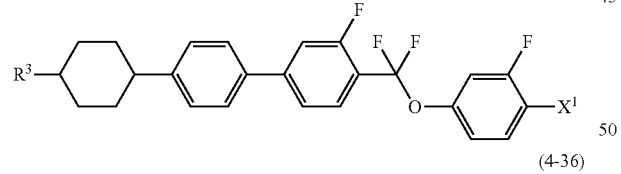
(4-36)
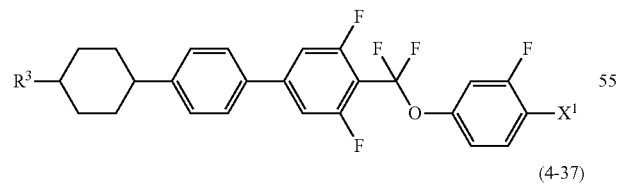
(4-37)
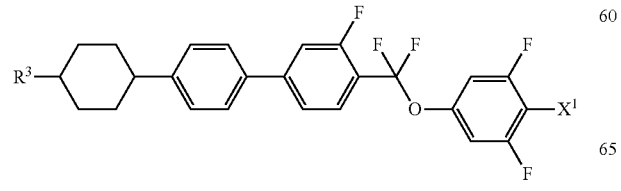
(4-38)
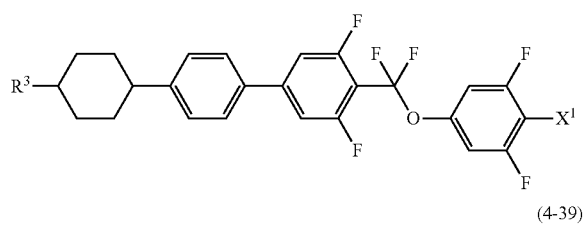
(4-39)
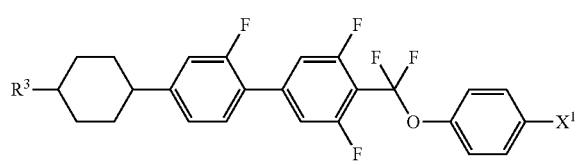
(4-40)
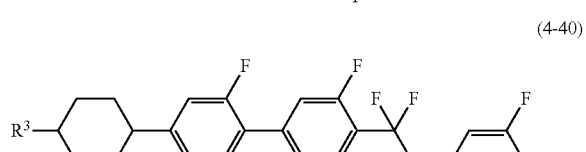
(4-41)
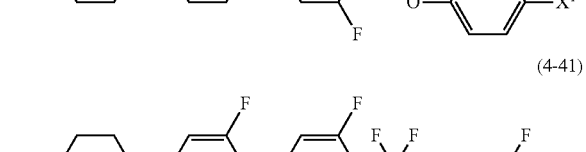
(4-42)
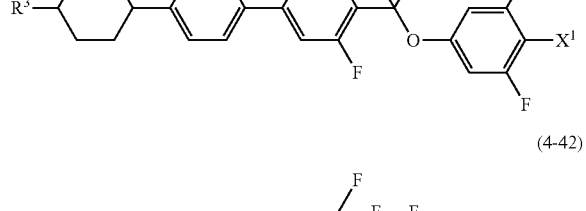
(4-43)
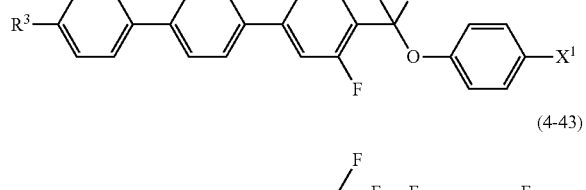
(4-44)
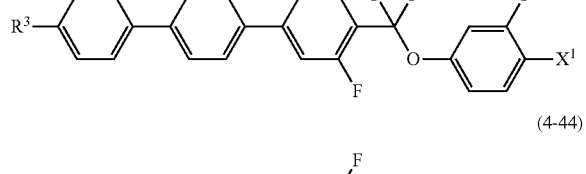
(4-45)
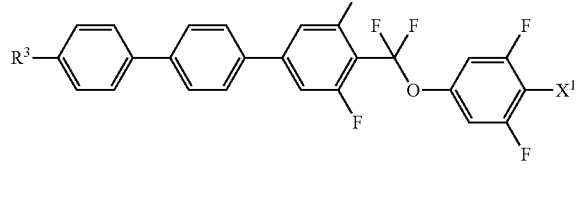
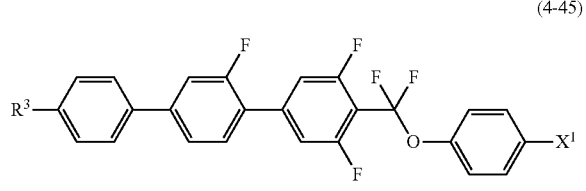

(4-46)
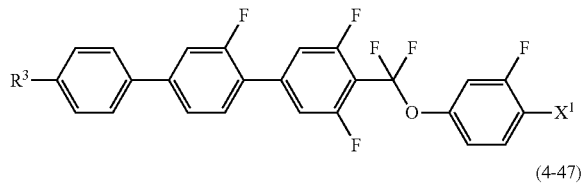

(4-47)
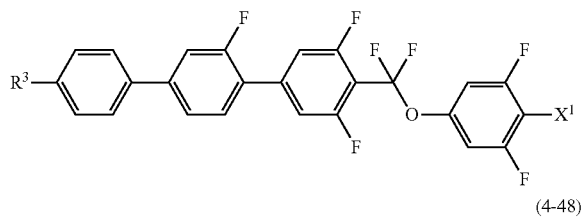

(4-48)
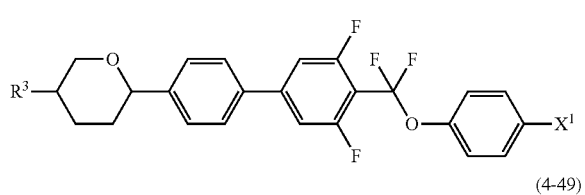

(4-49)
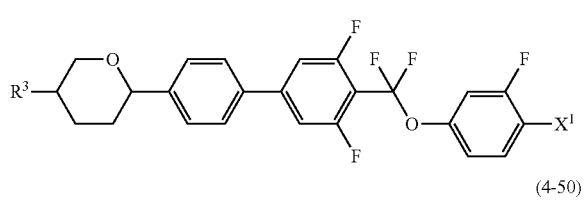

(4-50)
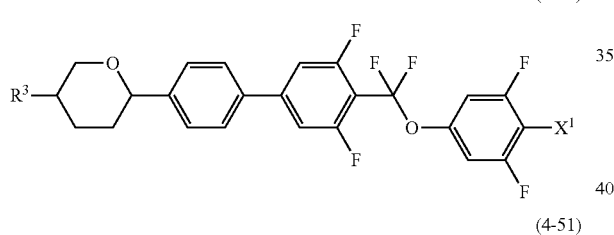

(4-51)
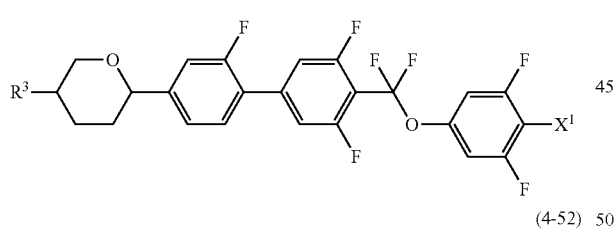

(4-52)
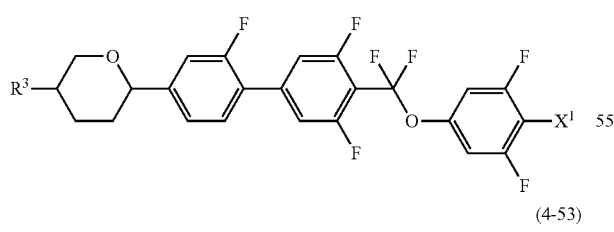

(4-53)
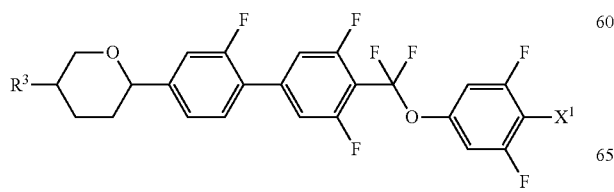

(4-54)
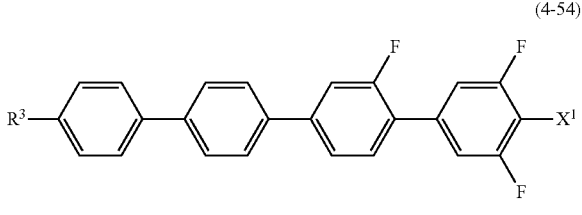

In the formulas, $R^3$ and $X^1$ are defined in the same way as described above.

Compounds (2) to (4), namely, component B, have a positive dielectric anisotropy value and an exceptional thermal stability and an exceptional chemical stability, and therefore are used when preparing a liquid crystal composition for use in a device having a TFT mode and a PSA mode. The content of component B in the liquid crystal composition of the invention is suitably in the range of approximately 1% by weight to approximately 99% by weight, preferably, in the range of approximately 10% by weight to approximately 97% by weight, further preferably, in the range of approximately 40% by weight to approximately 95% by weight, based on the total weight of the liquid crystal composition. Moreover, the viscosity can be adjusted by further allowing compounds (12) to (14) (component E) to be contained therein.

Suitable examples of compound (5), namely, component C, include compounds (5-1) to (5-64).

(5-1)
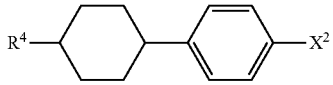

(5-2)

(5-3)
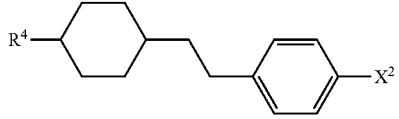

(5-4)
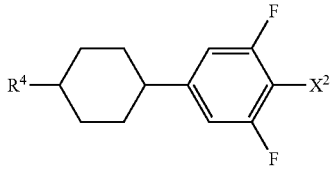

(5-5)
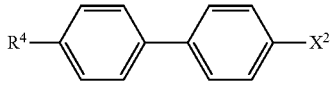

(5-6)
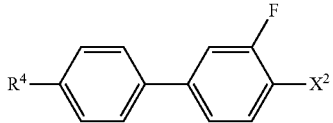

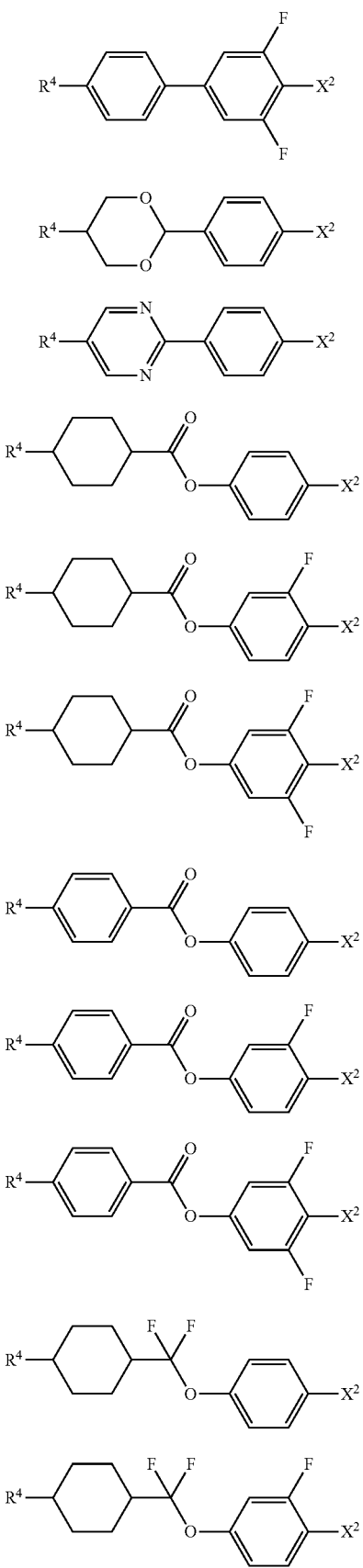
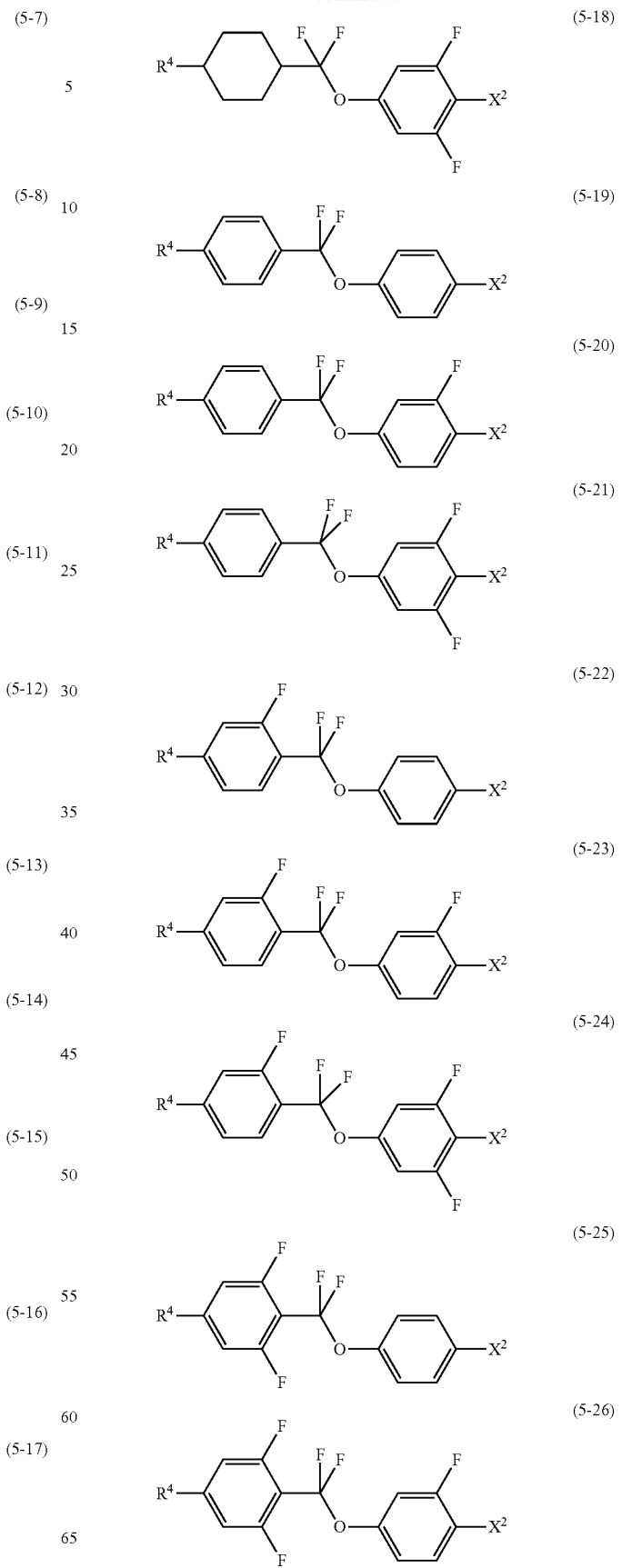

(5-27) 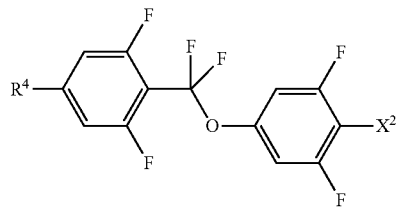
(5-28) 
(5-29) 
(5-30) 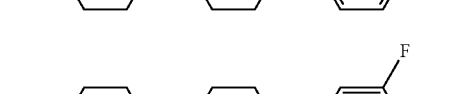
(5-31) 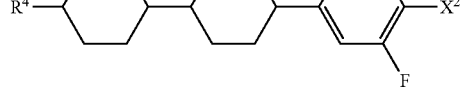
(5-32) 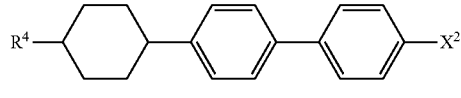
(5-33) 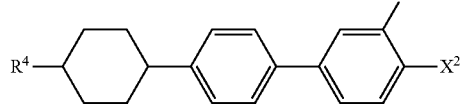
(5-34) 
(5-35) 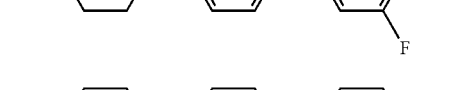
(5-36) 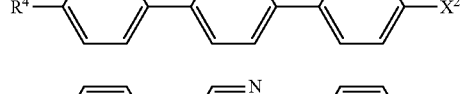
(5-37) 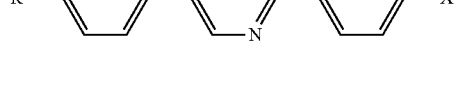
(5-38) 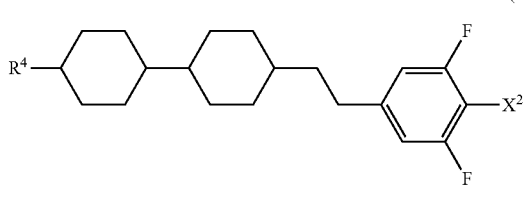
(5-39) 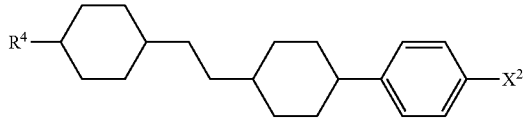
(5-40) 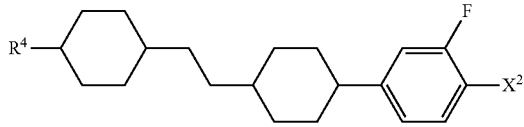
(5-41) 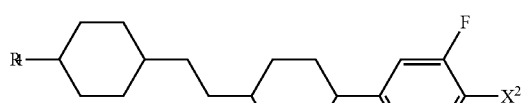
(5-42) 
(5-43) 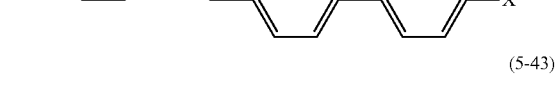
(5-44) 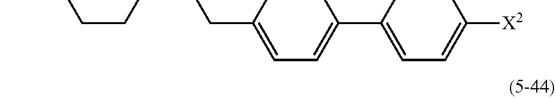
(5-45) 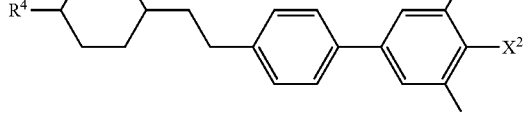
(5-46) 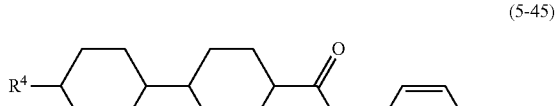

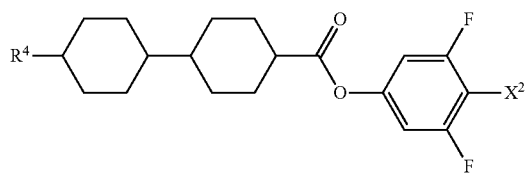
(5-47)
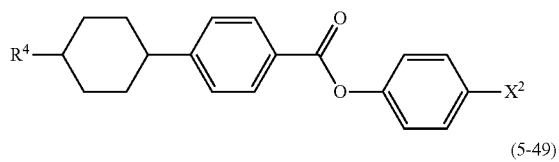
(5-48)
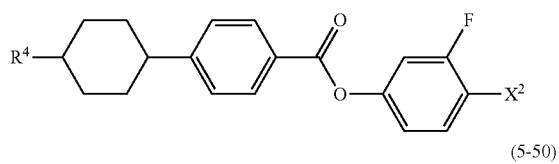
(5-49)
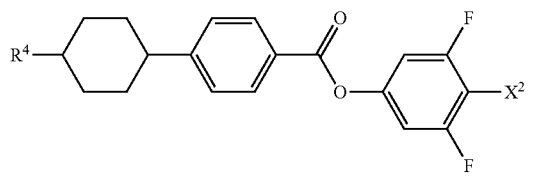
(5-50)
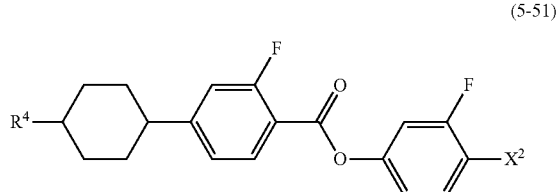
(5-51)
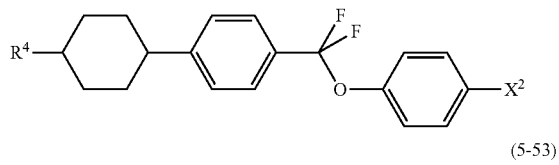
(5-52)
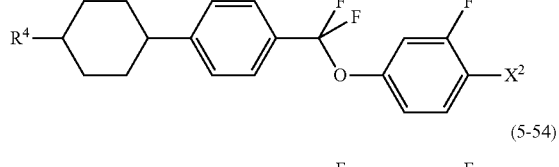
(5-53)
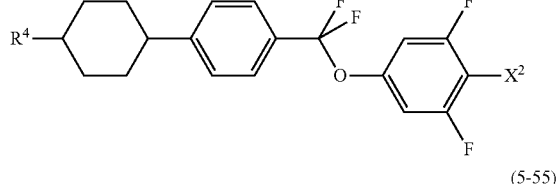
(5-54)
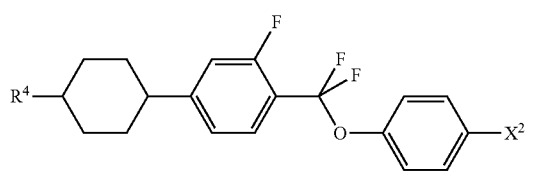
(5-55)
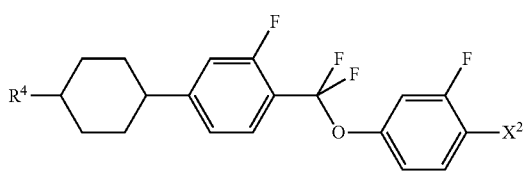
(5-56)
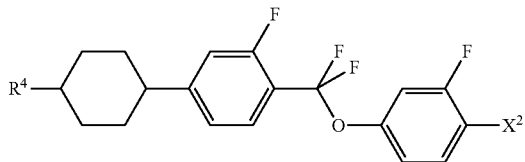
(5-57)
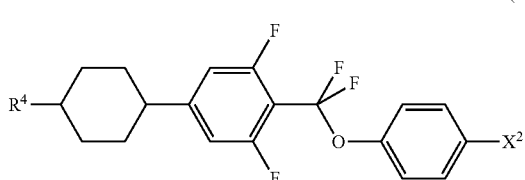
(5-58)
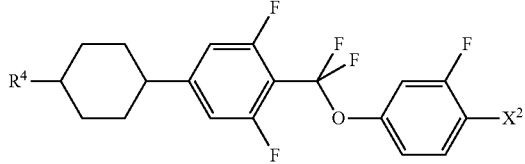
(5-59)
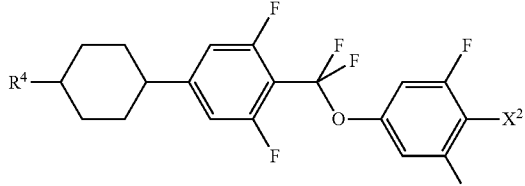
(5-60)
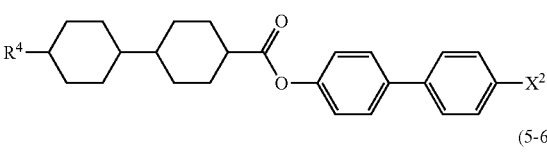
(5-61)
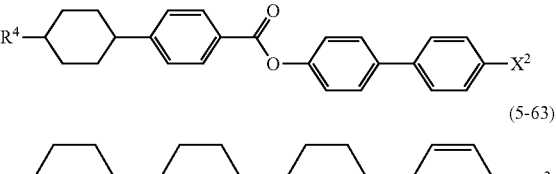
(5-62)
(5-63)
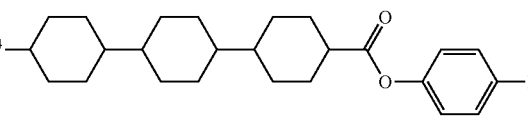
(5-64)

In the formulas, $R^4$ and $X^2$ are defined in the same way as described above.

Compound (5), namely, component C, has a positive and very large dielectric anisotropy value, and therefore is mainly used when preparing a liquid crystal composition for use in a device having an STN mode, a TN mode and a PSA mode. The threshold voltage of the composition can be decreased by allowing component C to be contained therein. Moreover, the viscosity and the refractive index anisotropy value can be adjusted, and the temperature range of the liquid crystal phase can be extended. Furthermore, component C can also be used for improvement of steepness.

When preparing the liquid crystal composition for use in the device having the STN mode or the TN mode, the content of component C is applicably in the range of approximately 0.1% by weight to approximately 99.9% by weight, preferably, in the range of approximately 10% by weight to approximately 97% by weight, further preferably, in the range of approximately 40% by weight to approximately 95% by weight. Moreover, the threshold voltage, the temperature range of the liquid crystal phase, the refractive index anisotropy value, the dielectric anisotropy value, the viscosity and so forth can be adjusted by mixing the component described later.

Component D including compounds (6) to (11) is preferred when preparing a liquid crystal composition having a negative dielectric anisotropy according to the invention to be used for a device having a vertical alignment mode (VA mode), a polymer sustained alignment mode (PSA mode) and so forth.

Suitable examples of compounds (6) to (11) (component D) include compounds (6-1) to (6-6), compounds (7-1) to (7-15), compound (8-1), compounds (9-1) to (9-3), compounds (10-1) to (10-11) and compounds (11-1) to (11-10).

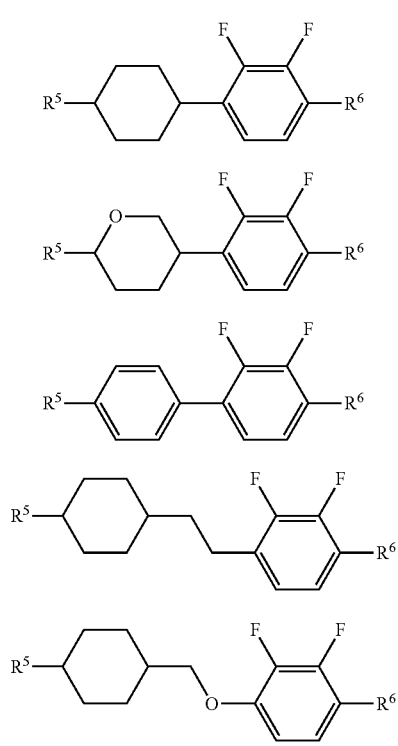

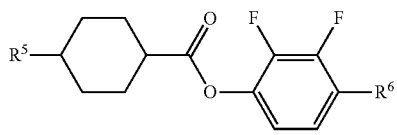

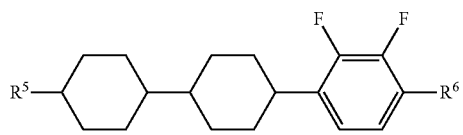

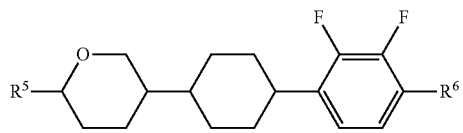

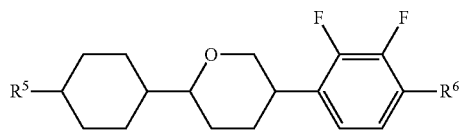

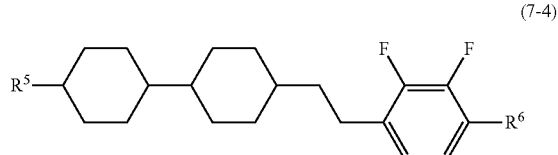

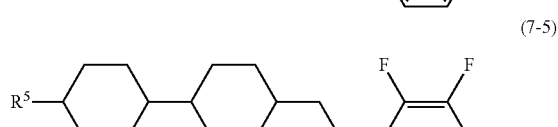

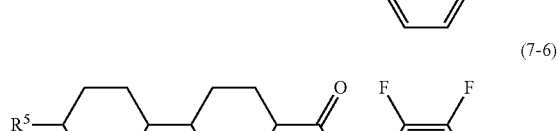

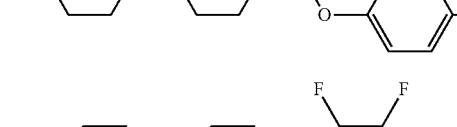

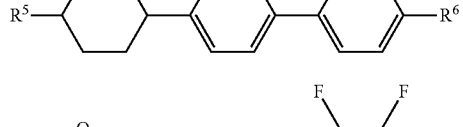

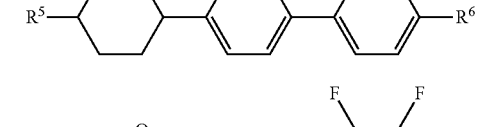

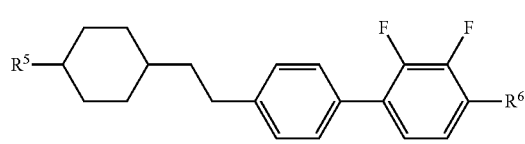
(7-11)
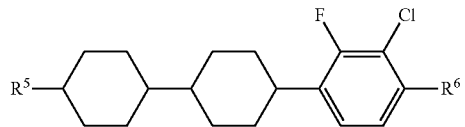
(7-12)
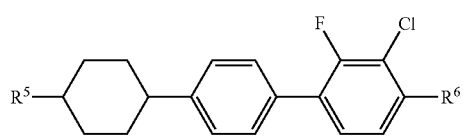
(7-13)
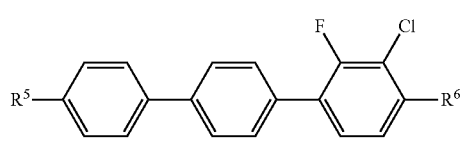
(7-14)
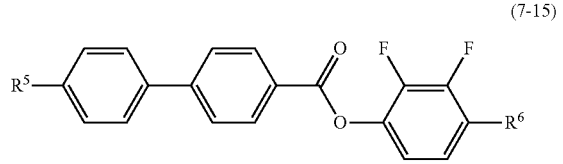
(7-15)
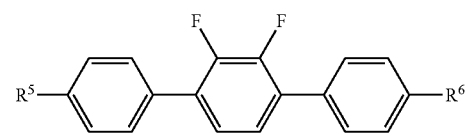
(8-1)
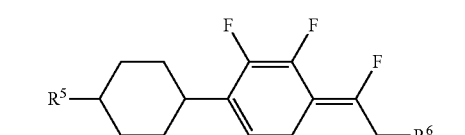
(9-1)
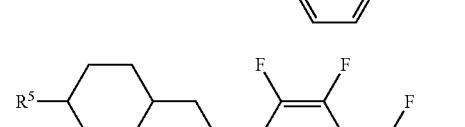
(9-2)
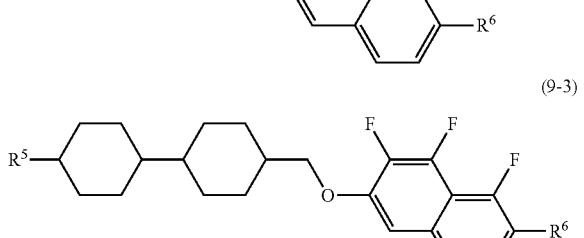
(9-3)
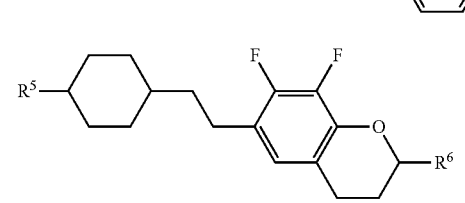
(10-1)
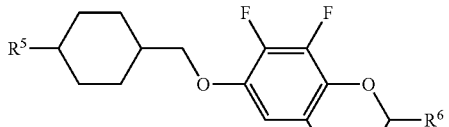
(10-2)
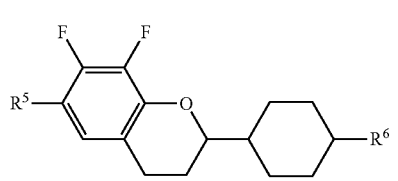
(10-3)
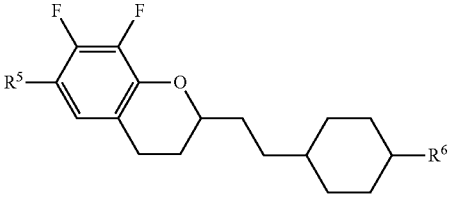
(10-4)
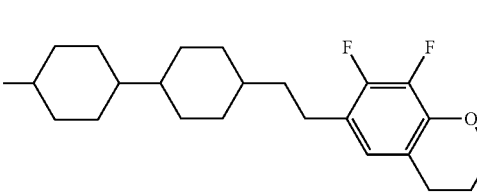
(10-5)
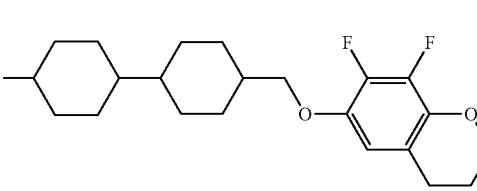
(10-6)
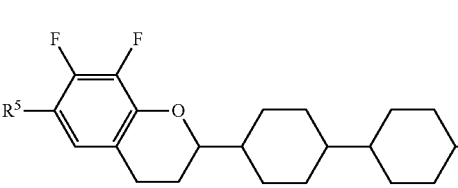
(10-7)
(10-8)
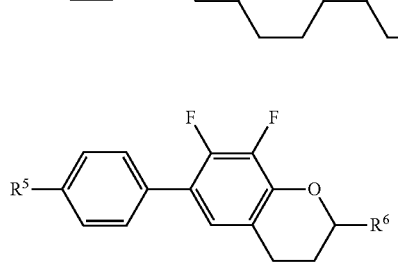
(10-9)

(10-10)
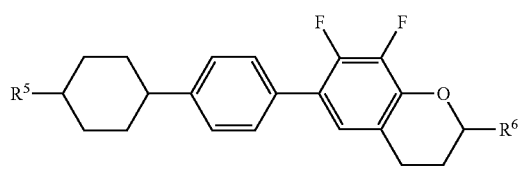

(10-11)
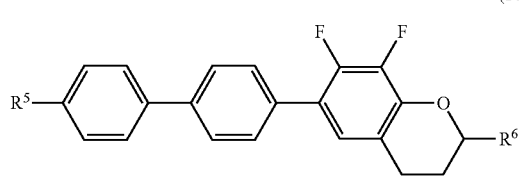

(11-1)
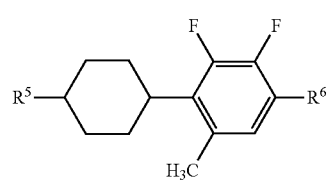

(11-2)
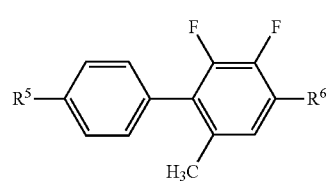

(11-3)
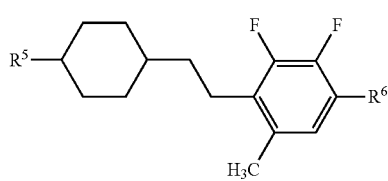

(11-4)
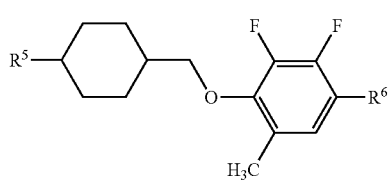

(11-5)
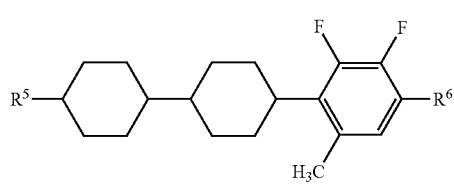

(11-6)
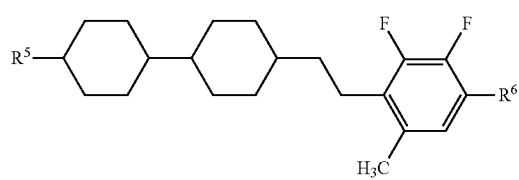

(11-7)
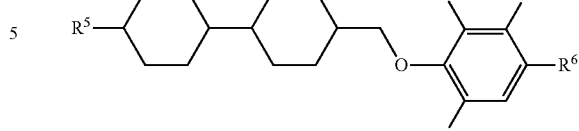

(11-8)

(11-9)
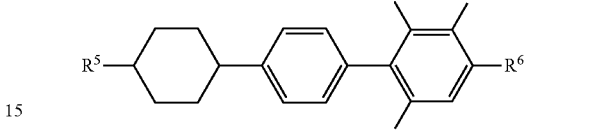

(11-10)

In the formulas, $R^5$ and $R^6$ are defined in the same way as described above.

The compounds of component D are mainly used for the composition having the negative dielectric anisotropy value for use in the device having the VA mode or the PSA mode. If the content is increased, the threshold voltage of the composition is decreased but the viscosity is increased, and therefore the content is preferably minimized as long as a required value of the threshold voltage is satisfied. However, if the content becomes less than approximately 40% by weight, voltage driving cannot be made in some cases because an absolute value of the dielectric anisotropy is approximately 5.

Because compound (6) in component D is a two-ring compound, compound (6) is mainly effective in adjusting the threshold voltage, the viscosity and the refractive index anisotropy value. Because compounds (7) and (8) are three-ring compounds, compounds (7) and (8) are effective in increasing the clearing point, extending a nematic range, decreasing the threshold voltage, increasing the refractive index anisotropy value and so forth. Compounds (9), (10) and (11) are effective in decreasing the threshold voltage and so forth.

When preparing the composition for use in the device having the VA mode or the PSA mode, the content of component D is preferably approximately 40% by weight or more, further preferably, in the range of approximately 50% by weight to approximately 95% by weight, based on the total weight of the composition. An elastic constant can be controlled to allow control of a voltage-transmission curve of the composition by mixing component D. When component D is mixed with a composition having a positive dielectric anisotropy value, the content of component D is preferably approximately 30% by weight or less based on the total weight of the composition.

Suitable examples of compounds (12), (13) and (14) (component E) include compounds (12-1) to (12-11), compounds (13-1) to (13-19) and compounds (14-1) to (14-6).
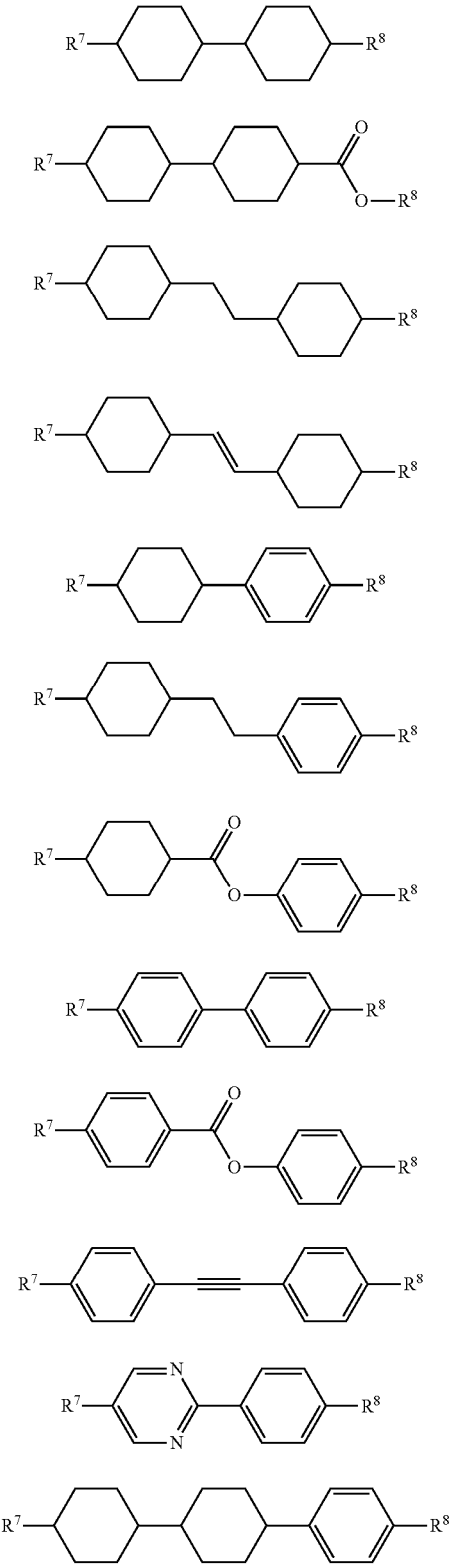
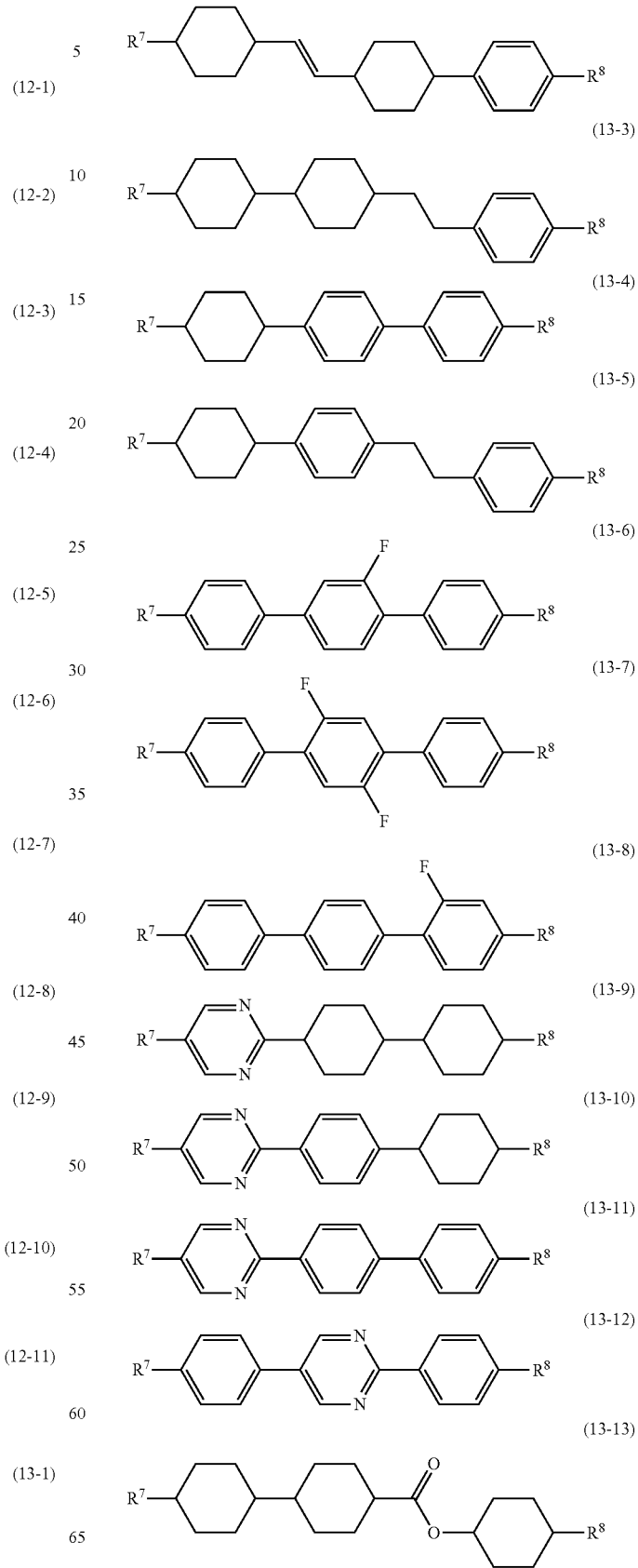

-continued (13-14)
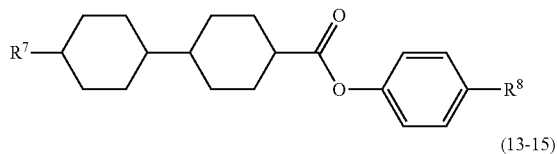

(13-15)
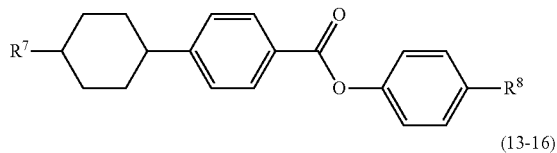

(13-16)
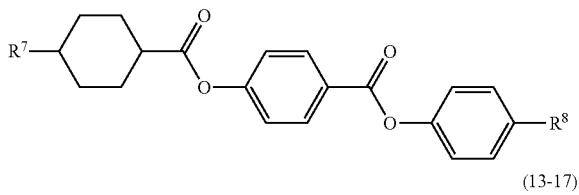

(13-17)
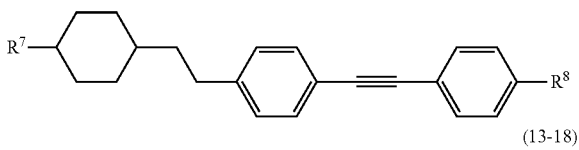

(13-18)
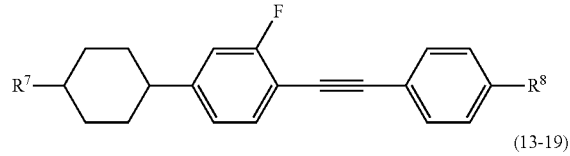

(13-19)
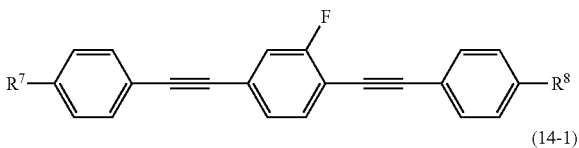

(14-1)
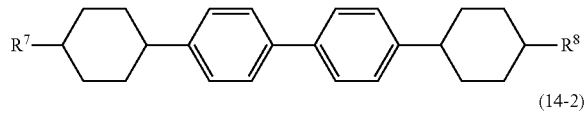

(14-2)
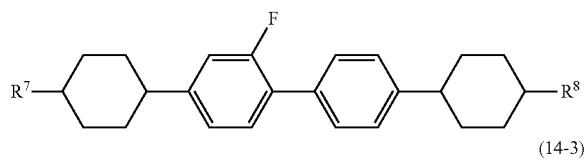

(14-3)
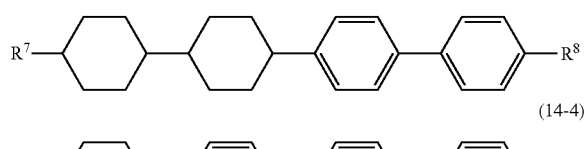

(14-4)
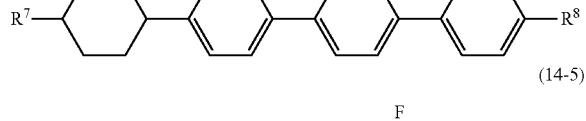

(14-5)

-continued (14-6)
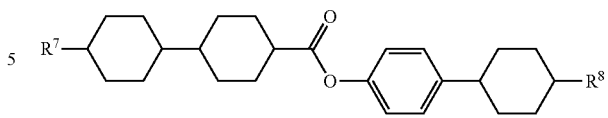

In the formulas, $R^7$ and $R^8$ are defined in the same way as described above.

Compounds (12) to (14) (component E) have a small absolute value of the dielectric anisotropy and are close to neutrality. Compound (12) is mainly effective in adjusting the viscosity or the refractive index anisotropy value. Compounds (13) and (14) are effective in extending the nematic range such as increasing the clearing point or adjusting the refractive index anisotropy value.

If the content of one of the compounds being component E is increased, the threshold voltage of the liquid crystal composition is increased and the viscosity thereof is decreased. Accordingly, the content is desirably maximized as long as a desired value of the threshold voltage of the liquid crystal composition is satisfied. When preparing the liquid crystal composition for use in the device having the TFT mode or the PSA mode, the content of component E is preferably approximately 30% by weight or more, further preferably, approximately 50% by weight or more, based on the total weight of the composition. When preparing the liquid crystal composition for use in the device having the TN mode, the STN mode or the PSA mode, the content of component E is preferably approximately 30% or more, further preferably, approximately 40% by weight or more, based on the total weight of the composition.

The liquid crystal composition of the invention preferably contains at least one of compound (1) of the invention in the range of approximately 0.1% by weight to approximately 99% by weight for developing excellent characteristics.

The liquid crystal composition of the invention is generally prepared according to a publicly known method, for example, a method for dissolving a required component under a high temperature. Moreover, an additive well known to those skilled in the art is added according to an application, and thus a liquid crystal composition containing an optically active compound, a polymerizable compound and a polymerization initiator as described below according to the invention, and a liquid crystal composition for use in a device having a guest host (GH) mode to which a dye is added can be prepared, for example. The additive is ordinarily well known to those skilled in the art, and is described in detail in literatures and so forth.

The liquid crystal composition of the invention may further contain at least one optically active compound therein.

A publicly known chiral dopant is added as the optically active compound. The chiral dopant is effective in inducing a helical structure of liquid crystals to adjust a twist angle as required and to prevent a reverse twist. Specific examples of the chiral dopant include optically active compounds (Op-1) to (Op-13) as described below.

(Op-1) 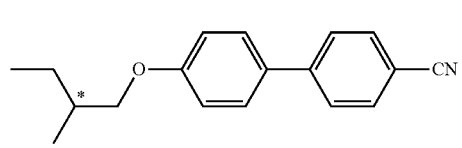
(Op-2) 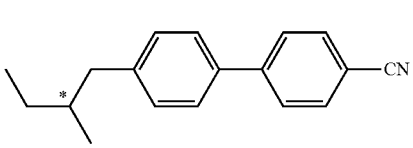
(Op-3) 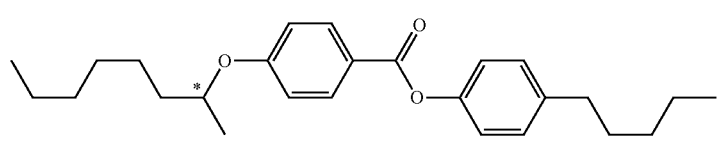
(Op-4) 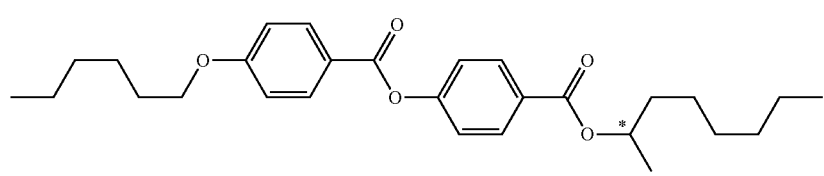
(Op-5) 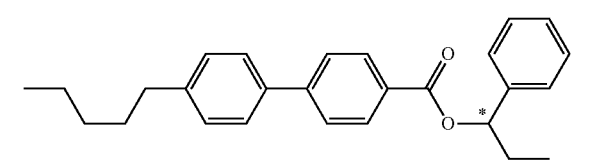
(Op-6) 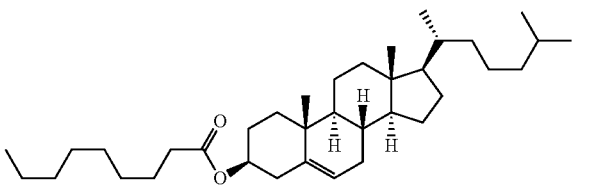
(Op-7) 
(Op-8) 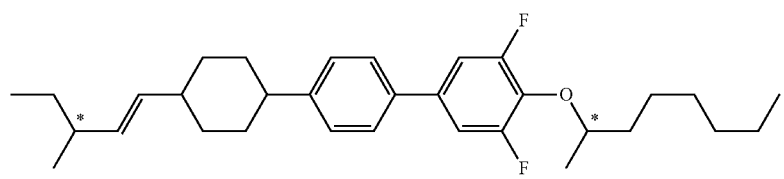
(Op-9) 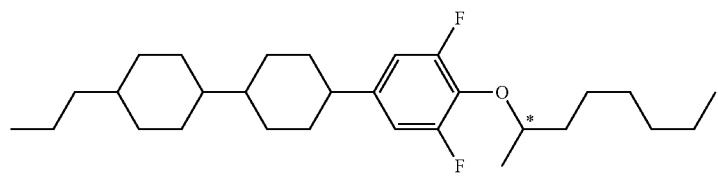
(Op-10) 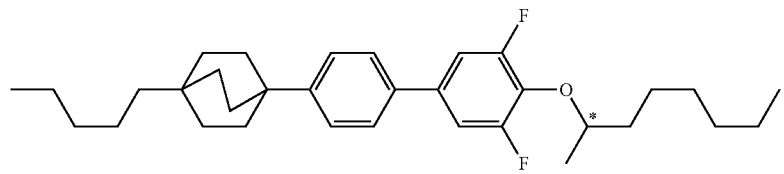

(Op-13)

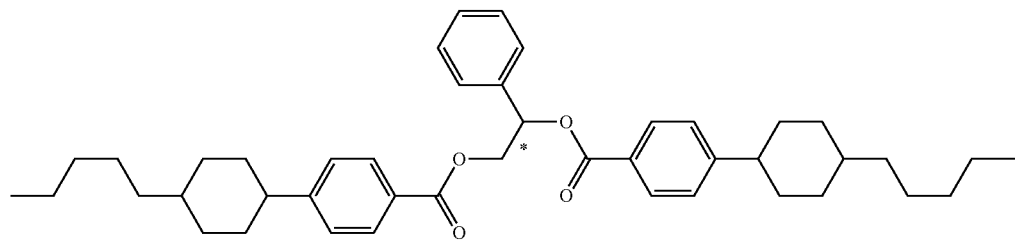

A helical pitch of the liquid crystal composition of the invention is ordinarily adjusted by adding the optically active compounds. The helical pitch is preferably adjusted in the range of approximately 40 micrometers to approximately 200 micrometers if the liquid crystal composition is for use in the device having the TFT mode and the TN mode. The helical pitch is preferably adjusted in the range of approximately 6 micrometers to approximately 20 micrometers if the liquid crystal composition is for use in the device having the STN mode. The helical pitch is preferably adjusted in the range of approximately 1.5 micrometers to approximately 4 micrometers if the liquid crystal composition is for use in a device having a bistable TN mode. Moreover, two or more kinds of optically active compounds may be added for the purpose of adjusting temperature dependence of the pitch.

If a dichroic dye such as a merocyanine, stylyl, azo, azomethine, azoxy, quinophthalone, anthraquinone or tetrazine dye is added, the liquid crystal composition of the invention can also be used as the liquid crystal composition for use in the device having the GH mode.

The liquid crystal composition of the invention can also be used as a composition for use in NCAP prepared by microencapsulating nematic liquid crystals, a polymer distributed liquid crystal display device (PDLCD) prepared by forming a three-dimensional network-polymer in liquid crystals, including a polymer network liquid crystal display device (PNLCD), and also for use in a device having an electrically controlled birefringence (ECB) mode or a DS mode.

The liquid crystal composition of the invention can also be used as the liquid crystal composition for use in the device having the polymer sustained alignment (PSA) mode by adding the polymerizable compound. Examples of the polymerizable compound include a compound having a polymerizable group such as acrylate, methacrylate, vinyl, vinyloxy, propenylether, epoxy, vinylketone and oxetane. The polymerizable compound is preferably polymerized by irradiation with ultraviolet light or the like in the presence of a suitable initiator such as a photopolymerization initiator. Suitable conditions for polymerization, suitable types of the initiator and suitable amounts thereof are known to those skilled in the art and are described in literatures. For example, Irgacure 651 (registered trademark), Irgacure 184 (registered trademark) or Darocure 1173 (registered trademark) (Ciba Japan K.K.), each being a photopolymerization initiator, is suitable for radical polymerization.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

In the following, the invention will be explained in more detail by way of Examples, but the invention is not limited by the Examples. A structure of a compound obtained was identified by an NMR spectrum, a mass spectrum or the like. Measurement was carried out according to methods described later. In each example, C stands for crystals, $S_A$ stands for a smectic A phase, $S_B$ stands for a smectic B phase, SX stands for a smectic phase having an unanalyzed phase structure, N stands for a nematic phase and Iso stands for an isotropic phase, and a unit of a phase transition temperature is expressed in terms of ° C. for all examples.

$^1$H-NMR Analysis:

DRX-500 (made by Bruker BioSpin Corporation) was used for measurement. Measurement was carried out using a solution prepared by dissolving a sample in a deuterated solvent such as $CDCl_3$ in which the sample was soluble, at room temperature by means of a nuclear magnetic resonance apparatus. Tetramethylsilane (TMS) was used as a reference material for a zero point of δ values.

Gas Chromatographic Analysis:

GC-14B gas chromatograph made by Shimadzu Corporation was used for measurement. A carrier gas was helium (2 mL per minute). A sample injector and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared as an acetone solution (0.1% by weight), and then 1 microliter of the solution was injected into the sample injector. A recorder was C-R6A Chromatopac made by Shimadzu Corporation or the equivalent thereof. A resulting gas chromatogram showed a retention time of a peak and a peak area corresponding to each of the component compounds.

Example 1

According to the synthetic scheme shown below, 4-((E)-2-fluorovinyl)-4'-((E)-prop-1-en-1-yl)-1,1'-bi(cyclohexane) (1-1) was prepared.

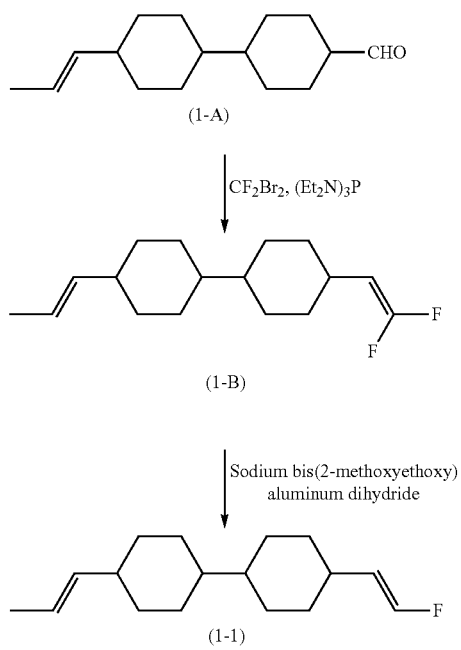

Synthesis of (E)-4-(2,2-difluorovinyl)-4'-(prop-1-en-1-yl)-1,1'-bi(cyclohexane) (1-B)

Difluorodibromomethane (29.9 g) was dissolved in THF (100 ml), and then a tris(diethylamino)phosphine (63.4 g) THF (20 ml) solution and an (E)-4'-(prop-1-en-1-yl)-[1,1'-bi(cyclohexane)]-4-carbaldehyde (20.0 g) THF (20 ml) solution were sequentially added dropwise in an ice bath under a nitrogen atmosphere. After completion of the reaction, 1 N hydrochloric acid was added, and extraction was carried out with toluene. An organic layer was washed with a saturated aqueous solution of sodium chloride, a saturated aqueous solution of sodium hydrogencarbonate and water, and then the resultant solution was dried over anhydrous magnesium sulfate and concentrated under reduced pressure, and thus a colorless oily matter was obtained. The resultant material was subjected to silica gel column chromatography (heptane) and recrystallization using Solmix A-11 (registered trademark) (Japan Alcohol Trading Co., Ltd.), and thus compound (1-B) was obtained as a white needle crystal (7.7 g).

Synthesis of 4-((E)-2-fluorovinyl)-4'-((E)-prop-1-en-1-yl)-1,1'-bi(cyclohexane) (1-1)

Compound (1-B) (5.0 g) obtained in the above operation was dissolved in toluene (50 ml), and a 65% sodium bis(2-methoxyethoxy)aluminum dihydride toluene solution (8.0 ml) was added dropwise. After completion of the reaction, 1N hydrochloric acid was added, and extraction was carried out with toluene. An organic layer was washed with a saturated aqueous solution of sodium chloride, a saturated aqueous solution of sodium hydrogencarbonate and water, and then the resultant solution was dried over anhydrous magnesium sulfate and concentrated under reduced pressure, and thus a colorless oily matter was obtained. The resultant material was subjected to silica gel column chromatography (heptane) and recrystallization at a low temperature by using Solmix A-11 (registered trademark) (Japan Alcohol Trading Co., Ltd.), and thus compound (1-1) was obtained as a colorless oily matter (1.2 g).

$^1$H NMR: δ: 6.48 (1H, dd, J=11.5, 86.4 Hz), 5.38-5.36 (2H, m), 5.29 (1H, ddd, J=8.0, 11.2, 19.5 Hz), 1.83-1.63 (13H, m), 1.09-1.01 (10H, m); $^{19}$F NMR: δ: 134.77 (1F, dd, J=20.1 85.9 Hz);

A phase transition temperature was C 0.1 N 101.9 Iso.

As described in paragraphs of Composition Examples below, a sample was prepared by mixing the compound (15% by weight) and mother liquid crystals A (85% by weight), and values of physical properties were calculated from values obtained by measurement, according to an extrapolation method: (extrapolated value)={(measured value of a sample)−0.85×(measured value of mother liquid crystals)}/0.15. The values of physical properties were determined as follows: NI=93.0° C., Δε=3.43, Δn=0.077, η=−7.7 mPa·s.

Example 2

In a manner similar to Example 1 in which the method was shown and the synthesis method was described, (E)-4-(2-fluorovinyl)-4'-vinyl-1,1'-bi(cyclohexane) (1-2) was obtained as a colorless needle crystal (3.1 g).

$^1$H NMR: δ: 6.49 (1H, dd, J=11.7, 98.1 Hz), 5.77 (1H, ddd, J=6.0, 10.0, 17.0 Hz), 5.29 (1H, ddd, J=8.0, 11.0, 19.5 Hz), 4.95 (1H, d, J=16.0 Hz), 4.87 (1H, d, J=9.0 Hz), 1.88-1.73 (10H, m), 1.11-1.00 (10H, m); $^{19}$F NMR: δ: 134.72 (1F, dd, J=20.2 85.9 Hz);

A phase transition temperature was C 1.0 N 61.3 Iso.

Values of physical properties were determined as follows: NI=60.4° C., Δε=1.97, Δn=0.0637, η=−17.1 mPa·s.

Example 3

The following compounds can be manufactured in a manner similar to Example 1.

Compound (1-3):

(E)-4-(but-3-en-1-yl)-4'-(2-fluorovinyl)-1,1'-bi(cyclohexane).

Compound (1-4):

4-((E)-2-fluorovinyl)-4'-((E)-pent-3-en-1-yl)-1,1'-bi(cyclohexane)

Example 4

Representative compositions of the invention were summarized in Composition Examples 2 to 11. First, the compound being a component of one of the compositions and the amount thereof (% by weight) were shown. The compound was described using symbols of a left-terminal group, a ring structure, a bonding group and a right-terminal group according to definitions in Table 1. A configuration of 1,4-cyclohexylene, tetrahydropyran-2,5-diyl and 1,3-dioxane-2,5-diyl is trans. When no symbol is described for a terminal group, the description represents that the terminal group is hydrogen. Next, the values of physical properties of the composition were shown.

TABLE

Method for Description of Compounds using
R—(A₁)—Z₁—...—Zₙ—(Aₙ)—R'

1) Left-terminal Group R— Symbol

| | |
|---|---|
| $C_nH_{2n+1}$— | n- |
| $C_nH_{2n+1}O$— | nO— |
| $C_mH_{2m+1}OC_nH_{2n}$— | mOn- |
| $CH_2=CH$— | V— |
| $C_nH_{2n+1}$—CH=CH— | nV— |
| $CH_2=CH$—$C_nH_{2n}$— | Vn- |
| $C_mH_{2m+1}$—CH=CH—$C_nH_{2n}$— | mVn- |
| $CF_2=CH$— | VFF— |
| $CF_2=CH$—$C_nH_{2n}$— | VFFn- |

2) Right-terminal Group —R' Symbol

| | |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —CH=$CF_2$ | —VFF |
| —$COOCH_3$ | -EMe |
| —CN | —C |
| —F | —F |
| —Cl | —CL |
| —$OCF_3$ | —OCF3 |
| —CH=CHF | —VF |

3) Bonding Grow —Zₙ— Symbol

| | |
|---|---|
| —$C_nH_{2n}$— | n |
| —COO— | E |
| —OCO— | e |
| —CH=CH— | V |
| —$CH_2O$— | 10 |
| —$CF_2O$— | X |
| —C≡C— | T |

4) Ring Structure —Aₙ— Symbol

 H

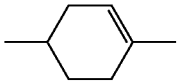 Ch

 Cx

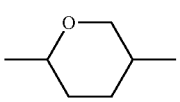 Dh

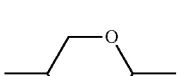 G

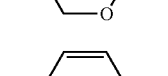 B

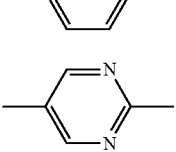 Py

TABLE-continued

Method for Description of Compounds using
R—(A₁)—Z₁—...—Zₙ—(Aₙ)—R'

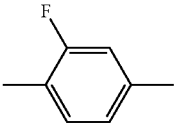 B(2F)

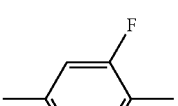 B(F)

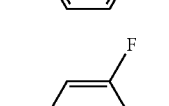 B(F,F)

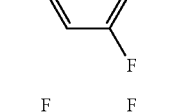 B(2F,3F)

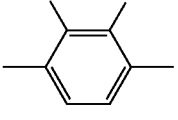 B(2F,3CL)

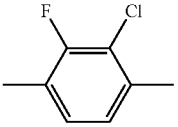 B(2CF3,3F)

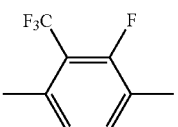 B(2CF2H,3F)

5) Examples of Description

Example 1
1V-HH-VF

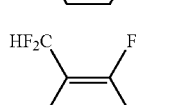

Ex. 2
3-HHB(2F,3F)-O2

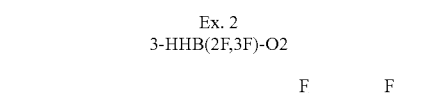

Example 3
3-HHB-3

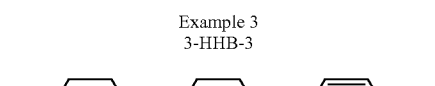

TABLE-continued

Method for Description of Compounds using
R—(A$_1$)—Z$_1$— ... —Z$_n$—(A$_n$)—R'

Example 4
3-HH-2

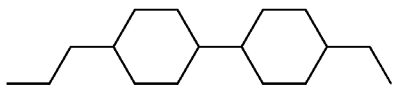

One example of the representative compositions of the invention is shown below. The values of physical properties of the compound were determined according to the methods described later.

Composition Example 1

Composition A (mother liquid crystals) having a nematic phase was prepared by mixing four compounds.
The four compounds are as described below:
4-(4-propylcyclohexyl)benzonitrile (24%);
4-(4-pentylcyclohexyl)benzonitrile (36%);
4-(4-heptylcyclohexyl)benzonitrile (25%); and
4-(4-pentylcyclohexyl)-4'-cyanobiphenyl (15%).
Values of physical properties of composition A were determined as described below: maximum temperature (NI)=71.7° C.; viscosity ($\eta_{20}$)=27.0 mPa·s; optical anisotropy ($\Delta$n)=0.137; dielectric anisotropy ($\Delta\in$)=11.0.
A composition was prepared by adding to composition A 15% by weight of 4-((E)-2-fluorovinyl)-4'-((E)-prop-1-en-1-yl)-1,1'-bi(cyclohexane) (1-1) as described in Example 1, and physical properties of the composition were measured.
As a result, values of the physical properties were determined as follows: maximum temperature (NI)=74.9° C.; optical anisotropy ($\Delta$n)=0.128; dielectric anisotropy ($\Delta\in$)=10.8.

Comparative Example 1

A composition including 85% of composition A as described in Composition Example 1 and 15% of (E)-4-(2-fluorovinyl)-4'-propyl-1,1'-bi(cyclohexane) (S-1) was prepared, and physical properties of the composition were measured.
Values of the physical properties were determined as follows: maximum temperature (NI)=72.1° C.; optical anisotropy ($\Delta$n)=0.125; dielectric anisotropy ($\Delta\in$)=9.8. Moreover, a phase transition temperature of compound (S-1) was C –10 S$_B$ 43.6 N 78.4 Iso. The values indicate that a temperature range of the nematic phase is narrower, the maximum temperature is lower and the dielectric anisotropy is smaller, as compared with the values of physical properties of compound (1-1).

Comparative Example 2

A composition including 85% of composition A as described in Composition Example 1 and 15% of 4-(2,2-difluorovinyl)-4'-propyl-1,1'-bi(cyclohexane) (S-4) was prepared, and physical properties of the composition were measured.
Values of the physical properties were determined as follows: maximum temperature (NI)=68.2° C.; optical anisotropy ($\Delta$n)=0.124; dielectric constant anisotropy ($\Delta\in$)=9.8. Moreover, a phase transition temperature of compound (S-4) was S$_B$ 39.5 N 42.6 Iso. The values indicate that the temperature range of the nematic phase is narrower, the maximum temperature is lower and the dielectric anisotropy is smaller, as compared with the values of physical properties of compound (1-1).

Comparative Example 3

A composition including 85% of composition A as described in Composition Example 1 and 15% of 4-propyl-4'-vinyl-1,1'-bi(cyclohexane) (S-5) was prepared, and physical properties of the composition were measured.
Values of the physical properties were determined as follows: maximum temperature (NI)=68.3° C.; optical anisotropy ($\Delta$n)=0.122; dielectric anisotropy ($\Delta\in$)=9.5. A phase transition temperature of compound (S-5) was C –23.9 S$_B$ 33.9 N 48.6 Iso. The values indicate that the temperature range of the nematic phase is narrower, the maximum temperature is lower and the dielectric anisotropy is smaller, as compared with the values of physical properties of compound (1-1).

Comparative Example 4

A composition including 85% of composition A as described in Composition Example 1 and 15% of (E)-4-(prop-1-en-1-yl)-4'-vinyl-1,1'-bi(cyclohexane) (S-6) was prepared, and physical properties of the composition were measured.
Values of the physical properties were determined as follows: maximum temperature (NI)=69.9° C.; optical anisotropy ($\Delta$n)=0.126; dielectric anisotropy ($\Delta\in$)=9.8. A phase transition temperature of compound (S-6) was C –17.8 S$_C$ 51.5 Iso. The values indicate that the nematic phase is absent, the maximum temperature is lower and the dielectric anisotropy is smaller, as compared with the values of physical properties of compound (1-1).

Characteristics can be measured according to the methods described below. Most of the methods are described in EIAJ ED-2521A of the Standard of Electronic Industries Association of Japan, or as modified thereon. TFT was not attached to a TN device used for measurement.

Transition Temperature (° C.):

Measurement was carried out according to any one of the following methods. 1) A sample was placed on a hot plate of a melting point apparatus equipped with a polarizing microscope (FP-52 Hot Stage made by Mettler Toledo International Inc.), and the sample was heated at a rate of 1° C. per minute. Temperature when a phase of the sample began to change was measured. 2) A scanning calorimeter Diamond DSC System made by PerkinElmer, Inc. was used, and measurement was carried out at a rate of 3° C. per minute.

The crystals were expressed as C. When the crystals were further distinguishable, each of the crystals was expressed as $C_1$ or $C_2$. The smectic phase was expressed as S. When a smectic B phase, a smectic C phase or a smectic A phase was distinguishable among the smectic phases, each of the phases was expressed as $S_B$, $S_C$ or $S_A$. The nematic phase was expressed as N. A liquid (isotropic) was expressed as Iso. As an expression of the phase transition temperature, "C 92.9 N 196.9 Iso" means that a transition temperature from the crystals to the nematic phase (CN) is 92.9° C., and a transition temperature from the nematic phase to the liquid (NI) is 196.9° C. A same rule applied to other expressions.

Maximum Temperature of a Nematic Phase (NI; ° C.):

A sample was placed on a hot plate in a melting point apparatus equipped with a polarizing microscope, and the sample was heated at a rate of 1° C. per minute. Temperature when a part of the sample began to change from a nematic phase to an isotropic liquid was measured. A higher limit of a temperature range of the nematic phase may be abbreviated as "maximum temperature."

Minimum Temperature of a Nematic Phase ($T_c$; ° C.):

A sample having the nematic phase was kept in freezers at temperatures of 0° C., −10° C., −20° C., −30° C. and −40° C. for 10 days, and then liquid crystal phases were observed. For example, when the sample maintained the nematic phase at −20° C. and changed to the crystals (or the smectic phase) at −30° C., $T_c$ was expressed as $T_c$<−20° C. A lower limit of the temperature range of the nematic phase may be abbreviated as "minimum temperature."

Compatibility of Compounds:

Mother liquid crystals having the nematic phase were prepared by mixing several compounds having a similar structure. A composition was obtained in which a compound to be measured and the mother liquid crystals were mixed. One example of a mixing ratio is 15% by weight of the compound and 85% by weight of the mother liquid crystals. The composition was kept at low temperatures such as −20° C. or −30° C. for 30 days. Whether or not a part of the composition changed to the crystals (or the smectic phase) was observed. A mixing ratio and a temperature for keeping the composition were changed as required. From the thus measured results, conditions were determined in which the crystals (or the smectic phase) precipitated or did not precipitate. The conditions are a measure of compatibility.

Viscosity (Bulk Viscosity; η; Measured at 20° C.; mPa·s):

A cone-plate (E type) viscometer was used for measurement.

Viscosity (Rotational Viscosity; γ1; Measured at 25° C.; mPa·s):

1) A Sample Having a Positive Dielectric Anisotropy:

Measurement was carried out according to the method described in M. Imai et al., Molecular Crystals and Liquid Crystals, Vol. 259, p. 37 (1995). The sample was put in a TN device in which a twist angle was 0 degrees and a distance (cell gap) between two glass substrates was 5 micrometers. A voltage was applied stepwise to the TN device in the range of 16 V to 19.5 V at an increment of 0.5 V. After a period of 0.2 second with no application, a voltage was applied repeatedly under the conditions of only one of rectangular waves (rectangular pulse; 0.2 second) and no application (2 seconds). A peak current and a peak time of a transient current generated by the application were measured. A value of the rotational viscosity was obtained from the measured value and a calculation equation (8) on page 40 of the paper presented by M. Imai et al. A value of the dielectric anisotropy required for the calculation was determined by the method for measuring the dielectric anisotropy described below by means of the device used in measuring the rotational viscosity.

2) A Sample Having a Negative Dielectric Anisotropy:

Measurement was carried out according to the method described in M. Imai et al., Molecular Crystals and Liquid Crystals, Vol. 259, p. 37 (1995). The sample was put in a VA device in which a distance (cell gap) between two glass substrates was 20 micrometers. A voltage was applied stepwise to the device in the range of 30 V to 50 V at an increment of 1 V. After a period of 0.2 second with no application, a voltage was applied repeatedly under the conditions of only one of rectangular waves (rectangular pulse; 0.2 second) and no application (2 seconds). A peak current and a peak time of a transient current generated by the application were measured. A value of the rotational viscosity was obtained from the measured value and a calculation equation (8) on page 40 of the paper presented by M. Imai et al. As the dielectric anisotropy required for the calculation, a value obtained according to the following dielectric anisotropy measurement was used.

Optical Anisotropy (Refractive Index Anisotropy; Δn; Measured at 25° C.):

Measurement was carried out by means of an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of the optical anisotropy was calculated from an equation: Δn=n∥−n⊥. When the sample was a composition, the optical anisotropy was measured by the method. When the sample was a compound, the optical anisotropy was measured after mixing the compound with a suitable composition. The optical anisotropy of the compound is expressed by an extrapolated value.

Dielectric Anisotropy (Δ∈; Measured at 25° C.):

When a sample was a compound, a dielectric anisotropy was measured after mixing the compound with a suitable composition. The dielectric anisotropy of the compound is expressed by an extrapolated value.

1) A Composition Having a Positive Dielectric Anisotropy:

A sample was put in a liquid crystal cell in which a distance (gap) between two glass substrates was 9 micrometers and a twist angle was 80 degrees. A voltage of 20 V was applied to the cell, and a dielectric constant (∈∥) in the major axis direction of liquid crystal molecules was measured. A voltage of 0.5 V was applied to the cell, and a dielectric constant (∈⊥) in the minor axis direction of the liquid crystal molecules was measured. A value of the dielectric anisotropy was calculated from an equation: Δ∈=∈∥−∈⊥.

2) A Composition Having a Negative Dielectric Anisotropy:

A sample was put in a liquid crystal cell subjected to homeotropic aligning treatment, a voltage of 0.5 V was applied, and a dielectric constant (∈∥) was measured. The sample was put in a liquid crystal cell subjected to homogeneous aligning treatment, a voltage of 0.5 V was applied, and a dielectric constant (∈⊥) was measured. A value of the dielectric anisotropy was calculated from the equation: Δ∈=∈∥−∈⊥.

Threshold Voltage (Vth; Measured at 25° C.; V):

When a sample was a compound, a threshold voltage was measured after mixing the compound with a suitable composition. The threshold voltage of the compound is expressed by an extrapolated value.

1) A Composition Having a Positive Dielectric Anisotropy:

A sample was placed in a normally white mode liquid crystal display device in which a distance (gap) between two glass substrates was (0.5/Δn) micrometers and a twist angle was 80 degrees. A Δn value is expressed by a value of the optical anisotropy measured by the method described above. Rectangular waves having a frequency of 32 Hz were applied to the device. A voltage of the rectangular waves was raised, and a value of voltage was measured when transmittance of light passing through the device reached 10%.

2) A Composition Having a Negative Dielectric Anisotropy:

A sample was put in a normally black mode liquid crystal display device subjected to homeotropic aligning treatment in which a distance (cell gap) between two glass substrates was 9 micrometers. Rectangular waves having a frequency of 32 Hz were applied to the device. A voltage of the rectangular waves was raised, and a value of voltage was measured when transmittance of light passing through the device reached 10%.

Voltage Holding Ratio (VHR; Measured at 25° C.; %):

A TN device used for measurement had a polyimide alignment film, and a distance (cell gap) between two glass substrates was 6 micrometers. A sample was put in the device, and then the device was sealed with an ultraviolet-polymerizable adhesive. The TN device was charged by applying a pulse voltage (60 microseconds at 5 V) thereto. A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

A ratio (percentage) of a component or a liquid crystal compound is expressed in terms of weight percent (% by weight) based on the total weight of the liquid crystal compound. The composition is prepared by measuring the weight of the components of the liquid crystal compound and so forth, and then mixing the components. Therefore, the weight percent of the component is easily calculated.

In measuring the characteristics, three methods are applied depending on a case where a single compound is used as a sample as is, a case where the compound is mixed with the mother liquid crystals and used as a sample, and a case where the composition is used as a sample as is. In the case where the compound is mixed with the mother liquid crystals, the method described below is applied. The sample was prepared by mixing 15% by weight of the compound and 85% by weight of the mother liquid crystals. The values of the characteristics were calculated from values obtained by measurement, according to the extrapolation method: (extrapolated value)={(measured value of a sample)−0.85×(measured value of mother liquid crystals)}/0.15. When the smectic phase (or crystals) precipitated at the above ratio at 25° C., a ratio of the compound to the mother liquid crystals was changed step by step in the order of (10% by weight:90% by weight), (5% by weight:95% by weight) and (1% by weight: 99% by weight).

Among the values obtained by measurement, a value obtained using the single compound as the sample as is, and a value obtained using the composition as the sample as it were directly described as experimental data. A value obtained using the compound mixed with the mother liquid crystals as the sample was directly described as experimental data in one case, or a value obtained according to the extrapolation method was described in another case.

As a solvent for diluting the sample, chloroform, hexane and so forth may also be used. The following capillary columns may also be used for separating the component compounds: Rtx-1 (length 30 m, bore 0.32 mm, film thickness 0.25 μm) made by Restek Corporation, and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds. A ratio of peak areas in a gas chromatogram corresponds to a ratio of the component compounds. The weight percent of the component compound is not completely identical with the ratio of the peak areas for each component. When the capillary columns described above are used in the invention, however, the weight percent of the component compound may be regarded as identical with the ratio of the peak areas for each component. The reason is that no large difference exists among correction coefficients of the component compounds.

Comparative Example 5

The composition contains a compound similar to compound (1-1). Components and characteristics of the composition were as described below.

| 3-HH-V | (S-6) similar to (1-1) | 8% |
| 5-HB-CL | (2-2) | 3% |
| 7-HB(F)-F | (2-3) | 7% |
| 3-HH-4 | (12-1) | 9% |
| 3-HH-EMe | (12-2) | 15% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

NI = 77.2° C.;
Δn = 0.064;
Δε = 5.8.

Composition Example 2

When compound (S-6) of the composition of Comparative Example 5 was replaced by compound (1-1), a composition of Composition Example 2 was found to be superior to the composition of Comparative Example 1 in having a higher maximum temperature (NI) and a larger dielectric anisotropy (Δ∈).

| 1V-HH-VF | (1-1) | 8% |
| 5-HB-CL | (2-2) | 3% |
| 7-HB(F)-F | (2-3) | 7% |
| 3-HH-4 | (12-1) | 9% |
| 3-HH-EMe | (12-2) | 15% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

NI = 80.0° C.;
Δn = 0.066;
Δε = 6.1.

Composition Example 3

| 1V-HH-VF | (1-1) | 3% |
| V-HH-VF | (1-2) | 5% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 14% |
| 3-HB-O2 | (12-5) | 4% |
| 3-HH-4 | (12-1) | 3% |
| 3-HHB-F | (3-1) | 3% |
| 3-HHB-1 | (13-1) | 8% |
| 3-HHB-O1 | (13-1) | 4% |
| 3-HBEB-F | (3-37) | 4% |
| 3-HHEB-F | (3-10) | 7% |
| 5-HHEB-F | (3-10) | 7% |
| 3-H2BTB-2 | (13-17) | 4% |
| 3-H2BTB-3 | (13-17) | 4% |

-continued

| | | |
|---|---|---|
| 3-H2BTB-4 | (13-17) | 4% |
| 3-HB(F)TB-2 | (13-18) | 5% |

NI = 93.5° C.;
Δn = 0.141;
Δε = 26.9;
η = 37.8 mPa · s.

Composition Example 4

| | | |
|---|---|---|
| 1V-HH-VF | (1-1) | 5% |
| V-HH-VF | (1-2) | 3% |
| 1V2-BEB(F,F)-C | (5-15) | 5% |
| 3-HB-C | (5-1) | 18% |
| 2-BTB-1 | (12-10) | 10% |
| 5-HH-VFF | (12-1) | 23% |
| 3-HHB-1 | (13-1) | 4% |
| VFF-HHB-1 | (13-1) | 8% |
| VFF2-HHB-1 | (13-1) | 11% |
| 3-H2BTB-2 | (13-17) | 5% |
| 3-H2BTB-3 | (13-17) | 4% |
| 3-H2BTB-4 | (13-17) | 4% |

NI = 84.3° C.;
Δn = 0.131;
Δε = 6.0;
η = 11.1 mPa · s.

Composition Example 5

| | | |
|---|---|---|
| 1V-HH-VF | (1-1) | 3% |
| V-HH-VF | (1-2) | 3% |
| 2-HB-C | (5-1) | 5% |
| 3-HB-C | (5-1) | 12% |
| 3-HB-O2 | (12-5) | 12% |
| 2-BTB-1 | (12-10) | 3% |
| 3-HHB-F | (3-1) | 4% |
| 3-HHB-1 | (13-1) | 8% |
| 3-HHB-O1 | (13-1) | 5% |
| 3-HHB-3 | (13-1) | 14% |
| 3-HHEB-F | (3-10) | 4% |
| 5-HHEB-F | (3-10) | 4% |
| 2-HHB(F)-F | (3-2) | 4% |
| 3-HHB(F)-F | (3-2) | 7% |
| 5-HHB(F)-F | (3-2) | 7% |
| 3-HHB(F,F)-F | (3-3) | 5% |

NI = 102.2° C.;
Δn = 0.100;
Δε = 4.5;
η = 16.6 mPa · s.

Composition Example 6

| | | |
|---|---|---|
| 1V-HH-VF | (1-1) | 4% |
| V-HH-VF | (1-2) | 3% |
| 5-HB-CL | (2-2) | 10% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (14-1) | 3% |
| 3-HHBB(F,F)-F | (4-6) | 2% |
| 4-HHBB(F,F)-F | (4-6) | 2% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 118.7° C.;
Δn = 0.090;
Δε = 3.5;
η = 18.1 mPa · s.

Composition Example 7

| | | |
|---|---|---|
| 1V-HH-VF | (1-1) | 5% |
| V-HH-VF | (1-2) | 5% |
| 3-HB-O1 | (12-5) | 14% |
| 3-HB(2F,3F)-O2 | (6-1) | 12% |
| 5-HB(2F,3F)-O2 | (6-1) | 10% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (13-1) | 4% |

NI = 87.6° C.;
Δn = 0.091;
η = 33.4 mPa · s;
Δε = −3.0.

Composition Example 8

| | | |
|---|---|---|
| 1V-HH-VF | (1-1) | 3% |
| V-HH-VF | (1-2) | 5% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 5-HHB(2F,3CL)-O2 | (7-12) | 2% |
| 3-HBB(2F,3F)-O2 | (7-7) | 9% |
| 5-HBB(2F,3F)-O2 | (7-7) | 9% |
| V-HHB-1 | (13-1) | 6% |
| 3-HHB-3 | (13-1) | 6% |
| 3-HHEBH-3 | (14-6) | 3% |
| 3-HHEBH-4 | (14-6) | 3% |
| 3-HHEBH-5 | (14-6) | 3% |

NI = 96.6° C.;
Δn = 0.100;
η = 28.5 mPa · s;
Δε = −3.8.

A pitch was 60.8 micrometers when 0.25 part by weight of optically active compound (Op-5) was added to 100 parts by weight of the composition described above.

Composition Example 9

| | | |
|---|---|---|
| 1V-HH-VF | (1-1) | 4% |
| V-HH-VF | (1-2) | 3% |
| 3-HB-O1 | (12-5) | 15% |
| 3-HB(2F,3F)-O2 | (6-1) | 12% |
| 5-HB(2F,3F)-O2 | (6-1) | 10% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |

-continued

| | | |
|---|---|---|
| 5-HHB(2F,3F)-O2 | (7-1) | 13% |
| 6-HEB(2F,3F)-O2 | (6-6) | 6% |

NI = 83.9° C.;
Δn = 0.089;
η = 33.0 mPa · s;
Δε = −3.4.

Composition Example 10

| | | |
|---|---|---|
| 1V-HH-VF | (1-1) | 14% |
| V-HH-VF | (1-2) | 8% |
| 3-HB-O2 | (12-5) | 12% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (13-1) | 3% |
| 3-HHB-3 | (13-1) | 4% |
| 3-HHB-O1 | (13-1) | 3% |

NI = 80.5° C.;
Δn = 0.102;
η = 17.9 mPa · s;
Δε = −3.5.

Composition Example 11

| | | |
|---|---|---|
| 1V-HH-VF | (1-1) | 3% |
| V-HH-VF | (1-2) | 6% |
| 3-HB-O1 | (12-5) | 12% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 11% |
| 3-HHB(2F,3F)-O2 | (7-1) | 13% |
| 5-HHB(2F,3F)-O2 | (7-1) | 13% |
| 3-HHB-1 | (13-1) | 6% |

NI = 88.4° C.;
Δn = 0.092;
η = 34.2 mPa · s;
Δε = −3.2.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

The invention provides a new liquid crystal compound including a fluorovinyl compound, and having a wide temperature range of a nematic phase, a low viscosity and an excellent compatibility with other liquid crystal materials.

The invention also provides a new liquid crystal composition comprising the features described above and having desired physical properties by using the liquid crystal compound as a component and suitably selecting a substituent and so forth constituting the compound, and further provides a liquid crystal display device constituted by using the liquid crystal composition.

What is claimed is:

1. A compound represented by formula (1):

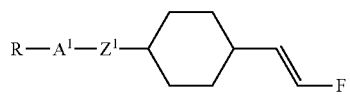

(1)

wherein R is alkenyl having 2 to 20 carbons; ring $A^1$ is 1,4-cyclohexylene or 1,4-phenylene in which at least one of hydrogen may be replaced by fluorine; and $Z^1$ is a single bond, —$CH_2CH_2$—, —CH=CH—, —$CH_2O$— or —$OCH_2$.

2. The compound according to claim 1, wherein, in formula (1), R is alkenyl having 2 to 20 carbons; and ring $A^1$ is 1,4-cyclohexylene, $Z^1$ is a single bond and n is 0.

3. A liquid crystal composition containing at least one compound according to claim 1.

4. The liquid crystal composition according to claim 3, further containing at least one compound selected from the group of compounds represented by formulas (2), (3) and (4):

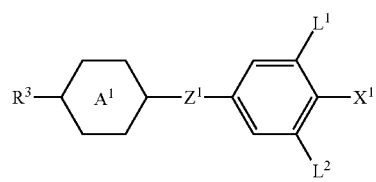

(2)

(3)

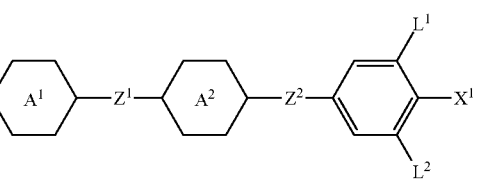

(4)

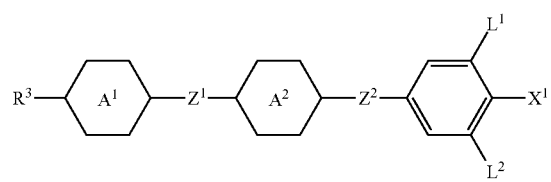

wherein $R^3$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^1$ is fluorine, chlorine, —$OCF_3$—, —$OCHF_2$—, —$CF_3$, —$CHF_2$, —$CH_2F$, —$OCF_2CHF_2$ or —$OCF_2CHFCF_3$;

ring $A^1$, ring $A^2$ and ring $A^3$ are independently 1,4-cyclohexylene, 1,3-dioxane-2,5-diyl, pyrimidine-2,5-diyl, 1-pyran-2,5-diyl, or 1,4-phenylene in which at least one of hydrogen may be replaced by fluorine;

$Z^1$ and $Z^2$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^1$ and $L^2$ are independently hydrogen or fluorine.

5. The liquid crystal composition according to claim 3, further containing at least one compound selected from the group of compounds represented by formula (5):

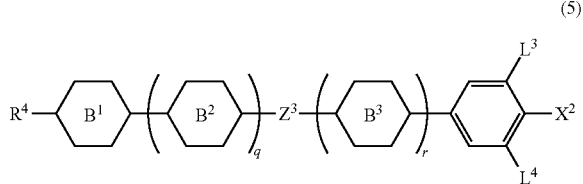

(5)

wherein $R^4$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^2$ is —CN or —C≡C—C≡N;

ring $B^1$, ring $B^2$ and ring $B^3$ are independently 1,4-cyclohexylene, 1,4-phenylene in which at least one of hydrogen may be replaced by fluorine, 1,3-dioxane-2,5-diyl, 1-pyran-2,5-diyl or pyrimidine-2,5-diyl;

$Z^3$ is —$(CH_2)_2$—, —COO—, —$CF_2O$—, —$OCF_2$—, —C≡C—, —$CH_2O$— or a single bond;

$L^3$ and $L^4$ are independently hydrogen or fluorine; and q is 0, 1 or 2, and r is 0 or 1.

6. The liquid crystal composition according claim 3, further containing at least one compound selected from the group of compounds represented by formulas (6), (7), (8), (9), (10) and (11):

wherein $R^5$ and $R^6$ are independently alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

ring $C^1$, ring $C^2$, ring $C^3$ and ring $C^4$ are independently 1,4-cyclohexylene, 1,4-cyclohexenylene, 1,4-phenylene in which at least one of hydrogen may be replaced by fluorine, 6-pyran-2,5-diyl or decahydro-2, 6-naphthalene;

$Z^4$, $Z^5$, $Z^6$ and $Z^7$ independently —$(CH_2)_2$—, —COO—, —$CH_2O$—, —$OCF_2$—, —$OCF_2(CH_2)_2$— or a single bond;

$L^5$ and $L^6$ are independently fluorine or chlorine; and j, k, l, m, n and p are independently 0 or 1, and a sum of k, l, m and n is 1 or 2.

7. The liquid crystal composition according to claim 3, further containing at least one compound selected from the group of compounds represented by formulas (12), (13) and (14):

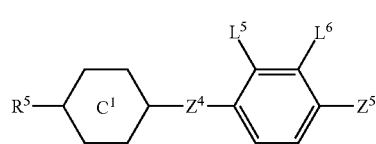

(6)

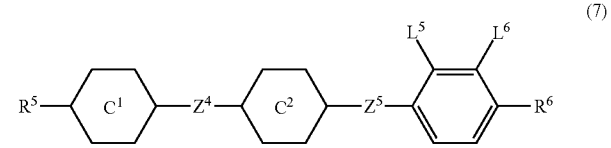

(7)

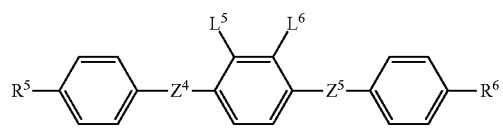

(8)

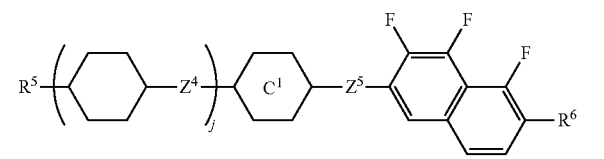

(9)

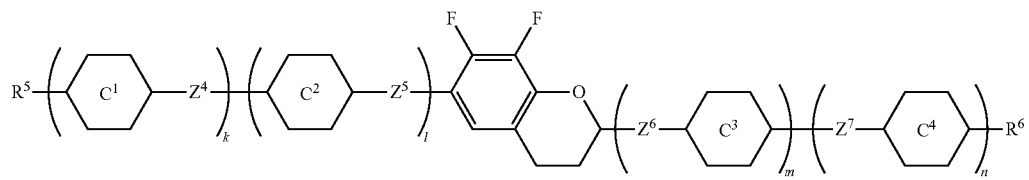

(10)

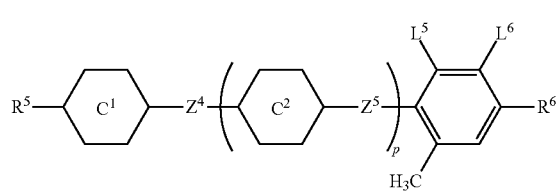

(11)

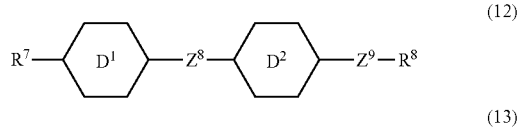
(12)

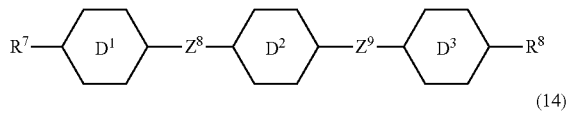
(13)

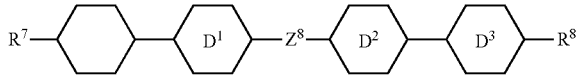
(14)

wherein $R^7$ and $R^8$ are independently alkyl having 1 to 10 carbons or alkenyl having 2 to 10 carbons, and in the alkyl and the alkenyl, at least one of —$CH_2$— may be replaced by —O— and at least one of hydrogen may be replaced by fluorine, excluding hydrogen in —CH=CHF;

ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^8$ and $Z^9$ are independently —C≡C—, —COO—, —$(CH_2)_2$—, —CH=CH— or a single bond.

8. The liquid crystal composition according to claim 4, further containing at least one compound selected from the group of compounds represented by formula (5) according to claim 5.

9. The liquid crystal composition according to claim 4, further containing at least one compound selected from the group of compounds represented by formulas (12), (13) and (14) according to claim 7.

10. The liquid crystal composition according to claim 5, further containing at least one compound selected from the group of compounds represented by formulas (12), (13) and (14) according to claim 7.

11. The liquid crystal composition according to claim 6, further containing at least one compound selected from the group of compounds represented by formulas (12), (13) and (14) according to claim 7.

12. The liquid crystal composition according to claim 3, further containing at least one optically active compound and/or at least one polymerizable compound.

13. The liquid crystal composition according to claim 3, further containing at least one antioxidant and/or at least one ultraviolet light absorber.

14. A liquid crystal display device containing the liquid crystal composition according to claim 3.

* * * * *